US010600973B2

(12) United States Patent
Miyazaki et al.

(10) Patent No.: US 10,600,973 B2
(45) Date of Patent: Mar. 24, 2020

(54) SYNTHETIC METHOD OF FUSED HETEROAROMATIC COMPOUND AND FUSED HETEROAROMATIC COMPOUND, AND INTERMEDIATE THEREOF

(71) Applicant: Samsung Electronics Co., Ltd., Suwon-si, Gyeonggi-do (KR)

(72) Inventors: Eigo Miyazaki, Hwaseong-si (KR); Jeong Il Park, Seongnam-si (KR); Hyun Bum Kang, Yongin-si (KR); Eun Kyung Lee, Seoul (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 0 days.

(21) Appl. No.: 16/033,574

(22) Filed: Jul. 12, 2018

(65) Prior Publication Data

US 2018/0323381 A1 Nov. 8, 2018

Related U.S. Application Data

(62) Division of application No. 15/392,816, filed on Dec. 28, 2016, now Pat. No. 10,056,563.

(30) Foreign Application Priority Data

Apr. 8, 2016 (KR) .................. 10-2016-0043689

(51) Int. Cl.

| | | |
|---|---|---|
| *H01L 51/00* | (2006.01) | |
| *H01L 51/05* | (2006.01) | |
| *H01L 51/50* | (2006.01) | |
| *C07D 333/74* | (2006.01) | |
| *C07D 345/00* | (2006.01) | |
| *C07D 495/00* | (2006.01) | |
| *C07D 495/22* | (2006.01) | |
| *C07D 517/22* | (2006.01) | |
| *C09K 11/06* | (2006.01) | |
| *C07D 495/04* | (2006.01) | |
| *C07D 517/04* | (2006.01) | |

(52) U.S. Cl.
CPC ........ *H01L 51/0074* (2013.01); *C07D 333/74* (2013.01); *C07D 345/00* (2013.01); *C07D 495/04* (2013.01); *C07D 495/22* (2013.01); *C07D 517/04* (2013.01); *C07D 517/22* (2013.01); *C09K 11/06* (2013.01); *H01L 51/0071* (2013.01); *H01L 51/0545* (2013.01); *H01L 51/0558* (2013.01)

(58) Field of Classification Search
CPC ............. H01L 51/0074; H01L 51/0071; H01L 51/0545; H01L 51/0558; H01L 51/50; H01L 51/05; C09K 11/06; C07D 517/04; C07D 495/04; C07D 345/00; C07D 333/74; C07D 495/22; C07D 517/22
See application file for complete search history.

(56) References Cited

U.S. PATENT DOCUMENTS

| | | | |
|---|---|---|---|
| 7,816,673 B2 | 10/2010 | Park et al. | |
| 2002/0019370 A1* | 2/2002 | Hegde ................. | A01N 43/653 |
| | | | 514/63 |
| 2009/0043113 A1 | 2/2009 | Park et al. | |
| 2010/0065826 A1 | 3/2010 | Takimiya et al. | |
| 2011/0166362 A1 | 7/2011 | Miyata et al. | |
| 2013/0330876 A1 | 12/2013 | Takimiya et al. | |
| 2014/0187792 A1 | 7/2014 | Ikeda et al. | |
| 2015/0239901 A1 | 8/2015 | Takimiya et al. | |
| 2016/0226005 A1 | 8/2016 | Park et al. | |
| 2017/0294593 A1 | 10/2017 | Miyazaki et al. | |

FOREIGN PATENT DOCUMENTS

| | | |
|---|---|---|
| EP | 2044076 | 4/2009 |
| EP | 2098527 A1 | 9/2009 |
| EP | 2679592 A1 | 1/2014 |
| EP | 2740735 A1 | 6/2014 |
| EP | 2889300 A1 | 7/2015 |
| EP | 3050887 A1 | 8/2016 |
| EP | 3228622 A2 | 10/2017 |
| JP | 2006-290192 A | 10/2006 |
| JP | 2009-152355 A | 7/2009 |
| JP | 2009-246140 A | 10/2009 |
| JP | 2011-184309 A | 9/2011 |
| JP | 2016050201 A * | 4/2016 |
| KR | 10-1314998 B1 | 10/2013 |
| KR | 10-2016-0093550 A | 8/2016 |
| WO | WO-2006/077888 A1 | 7/2006 |
| WO | WO-2009/0009790 A1 | 1/2009 |
| WO | WO-2011/132633 A1 | 10/2011 |
| WO | WO-2014/024769 A1 | 2/2014 |
| WO | WO-2015/137304 A1 | 9/2015 |

OTHER PUBLICATIONS

JP-2016050201-A; (2016) ProQuest English Machine Translation p. 1-57.*
Zhang, B., "Palladium-catalyzed highly regioselective 2-alkynylation of 2, x-dihalopyridines." Tetrahedron 72.22 (2016): 2813-2817.*
Calandra, N.A., "Development of enantioselective synthetic routes to the hasubanan and acutumine alkaloids." The Journal of organic chemistry 78.20 (2013): 10031-10057.*
Mizuta, S., "Redox chemistry of trifluoromethyl sulfonium salts as CF3 radical sources." Journal of Fluorine Chemistry 155 (2013): 124-131.*
Kadoya, N., "Palladium (II)-catalyzed asymmetric cycloisomerization of enynes for axially chiral biaryl construction." Tetrahedron Letters 54.6 (2013): 512-514.*

(Continued)

*Primary Examiner* — John M Mauro
(74) *Attorney, Agent, or Firm* — Harness, Dickey & Pierce, P.L.C.

(57) ABSTRACT

A method of synthesizing a fused heteroaromatic compound includes obtaining a first intermediate from a first compound represented by Chemical Formula 1 and a second compound represented by Chemical Formula 2, obtaining a second intermediate including a ring having a chalcogen element from the first intermediate, and obtaining a fused heteroaromatic compound by a cyclization reaction of the second intermediate.

12 Claims, 1 Drawing Sheet

(56) References Cited

OTHER PUBLICATIONS

Kadoya, N., "Palladium (II)-catalyzed asymmetric cycloisomerization of enynes for axially chiral biaryl construction." Tetrahedron Letters 54.6 (2013): 512-514; Supplemental Information p. 1-25.*
Cho, C-H. "Parallel synthesis of a desketoraloxifene analogue library via iodocyclization/palladium-catalyzed coupling." ACS combinatorial science 13.5 (2011): 501-510.*
Moslin, R. M., "Synthesis of conjugated polymers containing cis-phenylenevinylenes by titanium-mediated reductions." Macromolecules 42.1 (2008): 452-454.*
Moslin, R. M., "Synthesis of conjugated polymers containing cis-phenylenevinylenes by titanium-mediated reductions." Macromolecules 42.1 (2008): 452-454; Supplemental Information p. S1-S13.*
Bucinskas, A., "Synthesis, functionalization, and optical properties of chiral carbazole-based diaza [6] helicenes." The Journal of organic chemistry 80.5 (2015): 2521-2528.*
Nakano et al. "Isomerically Pure Anthra [2,3-b:6,7b']-difuran (anti-ADF), -dithiophene (anti-ADT), and -diselenophene (anti-ADS): Selective Synthesis, Electronic Structures, and Application to Organic Field-Effect Transistors," The Journal of Organic Chemistry, vol. 77, pp. 8099-8111 (2012).
Kienle, "Oxidative and Transition-Metal Catalyzed Cross-Coupling Reactions, Preparation and Coupling of S-Heterocycles," pp. 1-234 (2010).
Campeau et al., "Catalytic Direct Arylation with Aryl, Bromides, and Iodides: Intramolecular Studies Leading to New Intermolecular Reactions," J. Am. Chem. Soc. 2006, 128, pp. 581-590.
Yue et al., "Synthesis of 2,3-Disubstituted Benzo[b]thiophenes via Palladium-Catalyzed Coupling and Electrophilic Cyclization of Terminal Acetylenes," J. Org. Chem, 2002, 67, pp. 1905-1909.
Nakano et al., "Isometrically pure anthra[2,3-b:6,7-']-difuran (anti-ADF), -dithiophene (anti-ADT), and -diselenophene (anti-ADS): Selective synthesis, electronic structures, and application to organic field-effect transistors," Department of Applied Chemistry.
Partial European Search Report dated Jun. 13, 2017, for corresponding European Patent Application No. 17162097.4.
Truong, Minh Anh et al., "Synthesis of Benzofuro- and Indolo[3,2-b]indoles via Palladium-Catalyzed Double N-Arylation and Their Physical Properties", The Journal of Organic Chemistry, vol. 80, No. 22, Nov. 20, 2015, pp. 11566-11572, XP055374329, ISSN: 0022-3263, DOI: 10.1021/acs.joc.5b0286.
Takahashi, Motonobu et al, "Synthesis and Properties of Benzophospholo[3,2-b]benzofuran Derivatives", The Journal of Organic Chemistry, vol. 80, No. 8, Apr. 17, 2015, pp. 3790-3797, XP055374562, ISSN: 0022-3263, DOI: 10.1021/jo502889r.
Mehta, et al. "Iodine/Palladium Approaches to the Synthesis of Polyheterocyclic Compounds," J. Org. Chem., American Chemical Society, vol. 75, pp. 1652-1658 (2010).
Gopi, et al. "Synthesis of Fused Bromofurans via Mg-Mediated Dibromocyclopropanation of Cycloalkanone-Derived Chalcones and Cloke-Wilson Rearrangement," The Journal of Organic Chemistry, American Chemical Society, vol. 78, pp. 910-919 (2012).
Boyer, et al. "Domino rhodium(I)-catalysed reactions for the efficient synthesis of substituted benzofurans and indoles," Tetrahedron, Elsevier Science Publishers, vol. 66, pp. 6468-6482 (2010).
Saito, et al. "Facile synthesis of [1]benzothieno[3,2-b]benzothiophene from o-dihalostilbenes," Tetrahedron Letters, vol. 51, pp. 5277-5280 (2010).
Gwiazda, et al. "Highly Substitute Imidazole Derivatives from a New-Four Component Synthesis Employing Methoxyallene," Practical Synthetic Procedures, No. 6, pp. 0990-0994 (2008).
Harrowven, et al. "The synthesis of a Combretastatin A-4 Based Library and Discovery of New Cooperative ortho-Effects in Wittig Reactions Leading to (Z)-Stilbenes," Synlett Letter, No. 18, pp. 2977-2980 (2006).
Biniek "New Fused Bis-Thienobenzothienothiophene Copolymers and Their Use in Organic Solar Cells and Transistors," Macromolecules, American Chemical Society, vol. 46, pp. 727-735 (2013).

Kikumoto, et al. "Substituted (w-Aminoalkoxy)stilbene Derivatives as a New Class of Anticovulsants," J. Med. Chem., American Chemical Society, vol. 27, pp. 645-649 (1984).
Wan, et al. "Novel Ladder π-Conjugated Materials-Sila-Pentathienoacenes: Synthesis, Structure, and Electronic Properties," Chem. Asian. J., vol. 5, pp. 2290-2296 (2010).
Extended European Search Report dated Oct. 12, 2017, issued in corresponding European Application No. 17162097.4.
Tseng et al., "Synthesis and biological evaluation of novel symmetry bis-enediynes", European Journal of Medicinal Chemistry, 44 (2009) 35-41.
Konstantin Grenader et al.; Catalytic C—Se Bond Formation under Vey Mild Conditions for the Two-Step, One-Pot Synthesis of Aryl Selenoacetates; Adv. Synth. Catal.; 2012, pp. 2653-2658.
Hong Ahn et al.; :A Facile One-Pot Preparation of Organoselanyltrifluoroborates from Dihalobenzenes and Their Cross-Coupling Reaction; ,American Chemical Society; 2009 Organic Letters; Vo. 11, No. 2; pp. 361-364.
I.P. Beletskaya et al., "Tributyltin Aryl Selenides as Efficient Arylselenating Agents. Synthesis of Diaryl and Aryl Organyl Selenides" Russian Journal of Organic Chemistry, Vo. 37, No. 10, 2001, pp. 1463-1475.
Alain Krief et al.; "Reactions of Organic Selenocyanates with Hydroxides; The One-Pot Synthesis of Dialkyl Diselenides from Alkyl Bromides"; Agnew Chem. Int. Ed.; 2000; vol. 39; No. 9; pp. 1669-1672.
Marcelle Tiecco et al.; "Nucleohilic Aromatic Substitutions of Unactivated Aryl Halides by Methyl Selenide Anions. Synthesis and Selective Dealkylations of Aryl Alkyl Selenides." ;American Chemical Society; 1983 J. Org. Chem.; vol. 48; pp. 4289-4296.
Lars Engman et al.; A General Procedure for the Synthesis of Methylthio-Methylseleno- and Methyltelluro-Sunstituted Aromatic Compounds; Journal of Organometellic Chemistry; 1985; 296; pp. 357-366.
Marialuisa Aufiero et. al.; "Highly Efficient C—SeCF3 Coupling of Aryl I odides Enabled by an Air-Stable Dinucoear Pd Catalyst."; Agnew Chem Int. Ed.; 2015; 54; pp. 10322-10326.
Nakano, et al. "Isomerically Pure Anthra [2,3-b:6,7-b']-difuran (anti-ADF), -dithiophene (anti-ADT), and -diselenophene (anti-ADS): Selective Synthesis, Electronic Structures, and Application to Organic Field-Effect Transistors," The Journal of Organic Chemistry, vol. 77, No. 18, pp. 8099-8111 (2012).
Evers, et al. "New Synthetic Methods : Sodium Alkanechalcogenates As Demethylating Agents, Scope, Limitation and New One-Pot Synthesis of Diaryldiselenides," Tetrahedron Letters, vol. 24, No. 4, pp. 377-380 (1983).
Poon, et al. "In Search of Catalyic Antioxidants-(alkyltelluro)phenols, (Alkyltelluro)resorcinols, and Bis(alkyltelluro)phenols," The Journal of Organic Chemistry, vol. 78, pp. 6008-6015 (2013).
Grimaldi, et al. "(Biphenyl-2-alkyne) derivatives as common precursors for the synthesis of 9-iodo-10-organochalcogen-phenanthrenes and 9-organochalcogen-phenanthrenes," Organic & Biomolecular Chemistry, vol. 14, No. 44, pp. 10415-10426 (2016).
Luxen Andre, et al. "Synthese nouvelle et 15 rapide d'alkylseleno et alkylterluroarenes au moyen d'ethers-couronnes," Tetrahedron Letters, vol. 23, No. 38, pp. 3905-3908 (1982).
Mantovani, Anderson C., et al. "Chalcogenoalkynes: Precursors for the Regioselective Preparation of 2-Chalcogeno-1-halonaphthalenes through [4+2] Cycloaddition," European Journal of Organic Chemistry, pp. 4574-4579 (Retrieved from the CA Database online) (2012).
Gazizov, I.G. et al. "Thio- and selenoanisoles in complexation reactions with iodine," Chemical Abstracts Service, pp. 1-2 (Retrieved from the CA Database online) (1984).
Iwaoka, et al. "Physical-and Bio-Organic Chemistry on Nonbonded Selenium.cntdot . . . cntdot . . . cntdot.Oxygen Interactions," Chemical Abstracts Services, pp. 1 (Retrieved from the CA Database online) (2005).
Furin, et al. "15N, 17O, 31P and 77Se Nuclear Magnetic Resonance Spectra of Polyfluoroaromatic Compounds," Journal of Fluorine Chemistry, vol. 22, No. 3, pp. 231-252 (1983).

(56) References Cited

OTHER PUBLICATIONS

Evers, et al. "Aryl Arylazo sulfones chemistry. 2. Reactivity toward alkaline alkane-and arene selenolate and alkane- and arenetellurolate anions," Journal of Organic Chemistry, vol. 51, pp. 5196-5198 (1986).

European Search Report dated Apr. 5, 2018 issued in European Application No. 17199632.5.

Dong, H. "25th Anniversary Article: Key Points for High-Mobility Organic Field-Effect Transistors," Advanced Materials, vol. 25, No. 43, pp. 6158-6183 (2013).

Office Action for U.S. Appl. No. 15/645,257 dated Mar. 11, 2019.

Dorwald, Z., "Side Reactions in Organic Synthesis," Wiley-VCH Verlag GmbH & Co. KGaA, 2005.

U.S. Appl. No. 15/645,257, filed Jul. 10, 2017.

Office Action dated Oct. 9, 2019, issued in corresponding U.S. Appl. No. 15/645,257.

G. Dai et al., 'Z-Shaped Pentaleno-Acene Dimers with High Stability and Small Band Gap' *Angewandte Chemie, Intl, Ed.*, vol. 55, No. 8, Feb. 2016, pp. 2693-2696.

T. Hamura et al., 'Catalytic Generation of Arynes and Trapping by Nucleophilic Addition and Iodination' *Angewandte Chemie Intl. Ed.*, vol. 51, No. 14, Apr. 2012, pp. 3368-3372.

O. R'kyek et al., 'A General Palladium-Catalyzed Sonogashira Coupling of Aryl and Heteroaryl Tosylates' *Chemistry—A European Journal*, vol. 16, No. 33, Sep. 2010, pp. 9986-9989.

Office Action dated Dec. 13, 2019, issued in corresponding European Patent Application No. 17162097.4.

\* cited by examiner

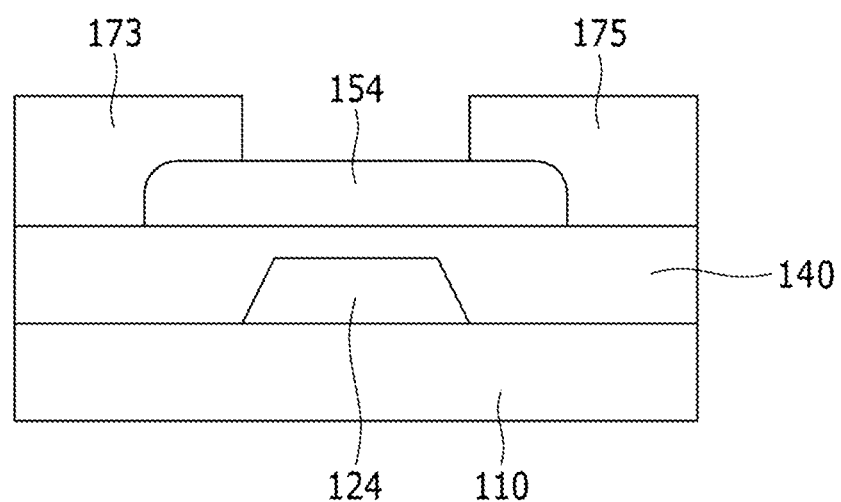

SYNTHETIC METHOD OF FUSED HETEROAROMATIC COMPOUND AND FUSED HETEROAROMATIC COMPOUND, AND INTERMEDIATE THEREOF

CROSS-REFERENCE TO RELATED APPLICATION

This application is a divisional of U.S. application Ser. No. 15/392,816, filed on Dec. 28, 2016, which claims priority to the benefit of Korean Patent Application No. 10-2016-0043689, filed in the Korean Intellectual Property Office on Apr. 8, 2016, the entire contents of each of the above-referenced applications are hereby incorporated by reference.

BACKGROUND

1. Field

Example embodiments provide a method of synthesizing a fused heteroaromatic compound, a fused heteroaromatic compound, and an intermediate thereof.

2. Description of the Related Art

A flat panel display (e.g., a liquid crystal display (LCD) or an organic light emitting diode (OLED) display) includes a thin film transistor (TFT) that is a three-terminal element as a switch. Research on an organic thin film transistor (OTFT) including an organic semiconductor (e.g., a low molecular semiconductor or polymer semiconductor) instead of an inorganic semiconductor (e.g., a silicon (Si) semiconductor) as one type of thin film transistor is being actively conducted. The organic thin film transistor may be made into a fiber or a film due to characteristics of an organic material, and thus is drawing attention as a core element for a flexible display device. The organic thin film transistor may be manufactured using a solution process (e.g., inkjet printing), and may be more easily applied to a large area flat panel display where a deposition process has a limit.

SUMMARY

Example embodiments provide a method of synthesizing a fused heteroaromatic compound that is applicable as an organic semiconductor.

Example embodiments also provide an intermediate of the fused heteroaromatic compound.

Example embodiments also provide a fused heteroaromatic compound prepared by the method.

Example embodiments also provide an electronic device including the fused heteroaromatic compound.

According to example embodiments, a method of synthesizing a fused heteroaromatic compound includes obtaining a first intermediate from a first compound represented by Chemical Formula 1 and a second compound represented by Chemical Formula 2, obtaining a second intermediate including a ring having a chalcogen element from the first intermediate, and obtaining a fused heteroaromatic compound by a cyclization reaction of the second intermediate:

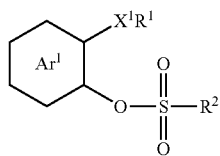

[Chemical Formula 1]

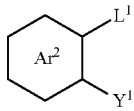

[Chemical Formula 2]

In Chemical Formula 1 or 2,
each of $Ar^1$ and $Ar^2$ are independently one of a substituted or unsubstituted aromatic ring, a substituted or unsubstituted heteroaromatic ring, and a fused ring of two or more rings therefrom,
$X^1$ is a chalcogen element,
each of $R^1$ and $R^2$ are independently one of hydrogen, a substituted or unsubstituted $C_1$ to $C_{20}$ alkyl group, a $C_1$ to $C_{20}$ fluoroalkyl group, a substituted or unsubstituted $C_6$ to $C_{20}$ aryl group, a halogen, and a combination thereof,
$L^1$ is one of an ethenyl group and an ethynyl group, and
$Y^1$ is a halogen.

The process of obtaining the first intermediate may include providing a halogen salt.

The process of obtaining the first intermediate may include providing one of potassium iodide, copper iodide, and a combination thereof.

The first compound may be represented by Chemical Formula 1a:

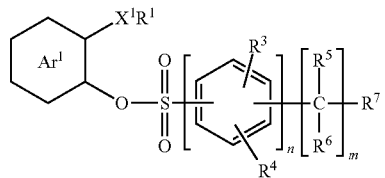

[Chemical Formula 1a]

In Chemical Formula 1a,
$Ar^1$ is one of a substituted or unsubstituted aromatic ring, a substituted or unsubstituted heteroaromatic ring, and a fused ring of two or more rings therefrom,
$X^1$ is a chalcogen element,
each of $R^1$ and $R^3$ to $R^7$ are independently one of hydrogen, a substituted or unsubstituted $C_1$ to $C_{20}$ alkyl group, a $C_1$ to $C_{20}$ fluoroalkyl group, a substituted or unsubstituted $C_6$ to $C_{20}$ aryl group, a halogen, and a combination thereof,
n is 0, 1, or 2, and
m is an integer ranging from 0 to 10.

The first compound may be represented by Chemical Formula 1aa.

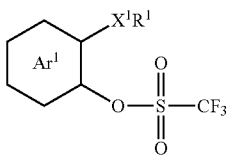

[Chemical Formula 1aa]

In Chemical Formula 1aa, $Ar^1$ is one of a substituted or unsubstituted aromatic ring, a substituted or unsubstituted heteroaromatic ring, and a fused ring of two or more rings therefrom, $X^1$ is a chalcogen element, and $R^1$ is one of hydrogen, a substituted or unsubstituted $C_1$ to $C_{20}$ alkyl group, a $C_1$ to $C_{20}$ fluoroalkyl group, a substituted or unsubstituted $C_6$ to $C_{20}$ aryl group, a halogen, and a combination thereof.

The process of obtaining the second intermediate may include providing a halogen molecule.

The process of obtaining the fused heteroaromatic compound may include providing a chalcogen element.

The first intermediate may be represented by Chemical Formula 3:

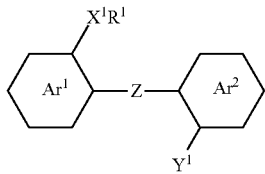

[Chemical Formula 3]

In Chemical Formula 3, each of $Ar^1$ and $Ar^2$ are independently one of a substituted or unsubstituted aromatic ring, a substituted or unsubstituted heteroaromatic ring, and a fused ring of two or more rings therefrom, $X^1$ is a chalcogen element, $R^1$ is independently one of hydrogen, a substituted or unsubstituted $C_1$ to $C_{20}$ alkyl group, a $C_1$ to $C_{20}$ fluoroalkyl group, a substituted or unsubstituted $C_6$ to $C_{20}$ aryl group, a halogen, and a combination thereof, Z is one of an ethene group and an ethyne group, and $Y^1$ is a halogen.

The second intermediate may be represented by Chemical Formula 4.

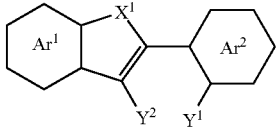

[Chemical Formula 4]

In Chemical Formula 4, each of $Ar^1$ and $Ar^2$ are independently one of a substituted or unsubstituted aromatic ring, a substituted or unsubstituted heteroaromatic ring, and a fused ring of two or more rings therefrom, $X^1$ is a chalcogen element, and each of $Y^1$ and $Y^2$ are independently a halogen.

The fused heteroaromatic compound may be represented by Chemical Formula 5.

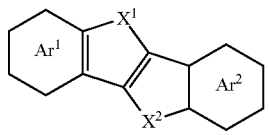

[Chemical Formula 5]

In Chemical Formula 5, each of $Ar^1$ and $Ar^2$ are independently one of a substituted or unsubstituted aromatic ring, a substituted or unsubstituted heteroaromatic ring, and a fused ring of two or more rings therefrom, and each of $X^1$ and $X^2$ are independently a chalcogen element.

The $Ar^1$ and $Ar^2$ may independently be one of a phenyl group, a naphthyl group, an anthracenyl group, a tetracenyl group, a pentacenyl group, a thiophenyl group, a selenophenyl group, a tellurophenyl group, a furanyl group, a pyrrolyl group, and a fused ring of two or more rings therefrom.

According to example embodiments, a fused heteroaromatic compound is prepared by the method of example embodiments.

According to example embodiments, an electronic device includes the fused heteroaromatic compound.

According to example embodiments, an intermediate is represented by Chemical Formula 3.

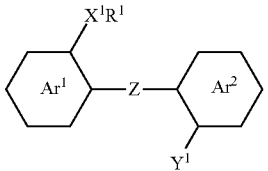

[Chemical Formula 3]

In Chemical Formula 3, each of $Ar^1$ and $Ar^2$ are independently one of a substituted or unsubstituted aromatic ring, a substituted or unsubstituted heteroaromatic ring, and a fused ring of two or more rings therefrom, $X^1$ is a chalcogen element, $R^1$ is one of hydrogen, a substituted or unsubstituted $C_1$ to $C_{20}$ alkyl group, a $C_1$ to $C_{20}$ fluoroalkyl group, a substituted or unsubstituted $C_6$ to $C_{20}$ aryl group, a halogen, and a combination thereof, Z is one of an ethene group and an ethyne group, and $Y^1$ is a halogen.

The $Ar^1$ and $Ar^2$ of Chemical Formula 3 may independently be one of a phenyl group, a naphthyl group, an anthracenyl group, a tetracenyl group, a pentacenyl group, a thiophenyl group, a selenophenyl group, a tellurophenyl group, a furanyl group, a pyrrolyl group, and a fused ring of two or more rings therefrom.

The intermediate represented by Chemical Formula 3 may be represented by Chemical Formula 3a.

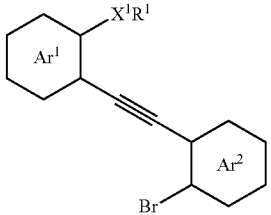

[Chemical Formula 3a]

In Chemical Formula 3a, each of $Ar^1$ and $Ar^2$ are independently one of a phenyl group, a naphthyl group, an anthracenyl group, a tetracenyl group, a pentacenyl group, a thiophenyl group, a selenophenyl group, a tellurophenyl group, a furanyl group, a pyrrolyl group, and a fused ring of two or more rings therefrom, $X^1$ is a chalcogen element, and $R^1$ is one of hydrogen, a substituted or unsubstituted $C_1$ to $C_{20}$ alkyl group, a $C_1$ to $C_{20}$ fluoroalkyl group, a substituted or unsubstituted $C_6$ to $C_{20}$ aryl group, a halogen, and a combination thereof.

According to example embodiments, a method of synthesizing an intermediate includes obtaining an intermediate represented by Chemical Formula 3 from a first compound represented by Chemical Formula 1 and a second compound represented by Chemical Formula 2.

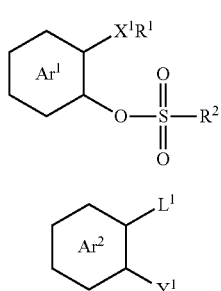

[Chemical Formula 1]

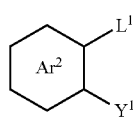

[Chemical Formula 2]

In Chemical Formula 1 or 2, each of $Ar^1$ and $Ar^2$ are independently one of a substituted or unsubstituted aromatic ring, a substituted or unsubstituted heteroaromatic ring, and a fused ring of two or more rings therefrom, $X^1$ is a chalcogen element, each of $R^1$ and $R^2$ are independently one of hydrogen, a substituted or unsubstituted $C_1$ to $C_{20}$ alkyl group, a $C_1$ to $C_{20}$ fluoroalkyl group, a substituted or unsubstituted $C_6$ to $C_{20}$ aryl group, a halogen, and a combination thereof, $L^1$ is one of an ethenyl group and an ethynyl group, and $Y^1$ is a halogen,

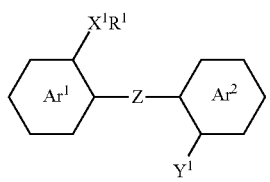

[Chemical Formula 3]

In Chemical Formula 3, each of $Ar^1$ and $Ar^2$ are independently one of a substituted or unsubstituted aromatic ring, a substituted or unsubstituted heteroaromatic ring, and a fused ring of two or more rings therefrom, $X^1$ is a chalcogen element, $R^1$ is independently one of hydrogen, a substituted or unsubstituted $C_1$ to $C_{20}$ alkyl group, a $C_1$ to $C_{20}$ fluoroalkyl group, a substituted or unsubstituted $C_6$ to $C_{20}$ aryl group, a halogen, and a combination thereof, Z is one of an ethene group and an ethyne group, and $Y^1$ is a halogen.

According to example embodiments, an intermediate is represented by Chemical Formula 4.

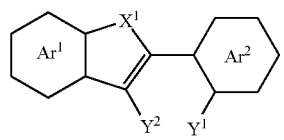

[Chemical Formula 4]

In Chemical Formula 4, each of $Ar^1$ and $Ar^2$ are independently one of a substituted or unsubstituted aromatic ring, a substituted or unsubstituted heteroaromatic ring, and a fused ring of two or more rings therefrom, $X^1$ is a chalcogen element, and each of $Y^1$ and $Y^2$ are independently a halogen.

The $Ar^1$ and $Ar^2$ of Chemical Formula 4 may independently be one of a phenyl group, a naphthyl group, an anthracenyl group, a tetracenyl group, a pentacenyl group, a thiophenyl group, a selenophenyl group, a tellurophenyl group, a furanyl group, a pyrrolyl group, and a fused ring of two or more rings therefrom.

The intermediate represented by Chemical Formula 4 may be represented by Chemical Formula 4a.

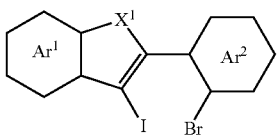

[Chemical Formula 4a]

In Chemical Formula 4a, each of $Ar^1$ and $Ar^2$ are independently one of a phenyl group, a naphthyl group, an anthracenyl group, a tetracenyl group, a pentacenyl group, a thiophenyl group, a selenophenyl group, a tellurophenyl group, a furanyl group, a pyrrolyl group, and a fused ring of two or more rings therefrom, and $X^1$ is a chalcogen element.

According to example embodiments, a method of synthesizing an intermediate includes obtaining a first intermediate from a first compound represented by Chemical Formula 1 and a second compound represented by Chemical Formula 2 and obtaining a second intermediate represented by Chemical Formula 4 from the first intermediate and a halogen molecule:

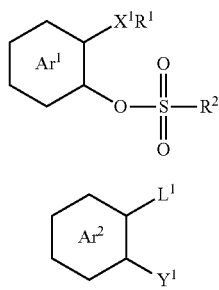

[Chemical Formula 1]

[Chemical Formula 2]

In Chemical Formulae 1 or 2, each of $Ar^1$ and $Ar^2$ are independently one of a substituted or unsubstituted aromatic ring, a substituted or unsubstituted heteroaromatic ring, and a fused ring of two or more rings therefrom, $X^1$ is a chalcogen element, each of $R^1$ and $R^2$ are independently one of hydrogen, a substituted or unsubstituted $C_1$ to $C_{20}$ alkyl group, a $C_1$ to $C_{20}$ fluoroalkyl group, a substituted or unsubstituted $C_6$ to $C_{20}$ aryl group, a halogen, and a combination thereof, $L^1$ is one of an ethenyl group and an ethynyl group, and $Y^1$ is a halogen, and

[Chemical Formula 4]

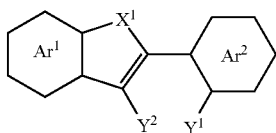

In Chemical Formula 4, each of $Ar^1$ and $Ar^2$ are independently one of a substituted or unsubstituted aromatic ring, a substituted or unsubstituted heteroaromatic ring, and a fused ring of two or more rings therefrom, $X^1$ is a chalcogen element, and each of $Y^1$ and $Y^2$ are independently a halogen.

BRIEF DESCRIPTION OF THE DRAWING

The FIGURE is a cross-sectional view of an organic thin film transistor according to example embodiments.

DETAILED DESCRIPTION

Example embodiments will hereinafter be described in detail, and may be more easily performed by those who have common knowledge in the related art. However, this disclosure may be embodied in many different forms and is not to be construed as limited to the example embodiments set forth herein.

It should be understood that, although the terms first, second, third, etc. may be used herein to describe various elements, components, regions, layers and/or sections, these elements, components, regions, layers, and/or sections should not be limited by these terms. These terms are only used to distinguish one element, component, region, layer, or section from another region, layer, or section. Thus, a first element, component, region, layer, or section discussed below could be termed a second element, component, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

As used herein, when a definition is not otherwise provided, the term 'substituted' refers to replacement by a substituent selected from a halogen atom, a hydroxy group, an alkoxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid group or a salt thereof, a $C_1$ to $C_{20}$ alkyl group, a $C_2$ to $C_{20}$ alkenyl group, a $C_2$ to $C_{20}$ alkynyl group, a $C_6$ to $C_{30}$ aryl group, a $C_7$ to $C_{30}$ arylalkyl group, a $C_1$ to $C_{30}$ alkoxy group, a $C_1$ to $C_{20}$ heteroalkyl group, a $C_3$ to $C_{20}$ heteroarylalkyl group, a $C_3$ to $C_{30}$ cycloalkyl group, a $C_3$ to $C_{15}$ cycloalkenyl group, a $C_6$ to $C_{15}$ cycloalkynyl group, a $C_3$ to $C_{30}$ heterocycloalkyl group, and a combination thereof, instead of hydrogen of a compound.

As used herein, when a definition is not otherwise provided, the term "hetero" refers to one including 1 to 4 heteroatoms selected from N, O, S, Se, Si, and P.

Hereinafter, a method of synthesizing a fused heteroaromatic compound according to example embodiments is described.

In a method of synthesizing a fused heteroaromatic compound according to example embodiments, an intermediate is obtained from novel reactants with a relatively high yield, and a fused heteroaromatic compound having a chalcogen element may be obtained from the intermediate with the relatively high yield.

A method of synthesizing a fused heteroaromatic compound according to example embodiments includes obtaining a first intermediate from an aromatic compound substituted with a chalcogen-containing group, obtaining a second intermediate including a ring having a chalcogen element from the first intermediate, and obtaining a fused heteroaromatic compound by a cyclization reaction of the second intermediate.

The process of obtaining the first intermediate may include reacting a first compound represented by Chemical Formula 1 with a second compound represented by Chemical Formula 2.

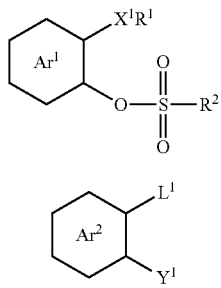

[Chemical Formula 1]

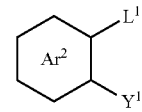

[Chemical Formula 2]

In Chemical Formula 1 or 2, each of $Ar^1$ and $Ar^2$ are independently one of a substituted or unsubstituted aromatic ring, a substituted or unsubstituted heteroaromatic ring, and a fused ring of two or more rings therefrom, $X^1$ is a chalcogen element, each of $R^1$ and $R^2$ are independently one of hydrogen, a substituted or unsubstituted $C_1$ to $C_{20}$ alkyl group, a $C_1$ to $C_{20}$ fluoroalkyl group, a substituted or unsubstituted $C_6$ to $C_{20}$ aryl group, a halogen, and a combination thereof, $L^1$ is one of an ethenyl group and an ethynyl group, and, $Y^1$ is a halogen.

The $Ar^1$ and $Ar^2$ may independently be one of a phenyl group, a naphthyl group, an anthracenyl group, a tetracenyl group, a pentacenyl group, a thiophenyl group, a selenophenyl group, a tellurophenyl group, a furanyl group, a pyrrolyl group, and a fused ring of two or more rings therefrom.

The $Ar^1$ and $Ar^2$ may be the same or different and may be, for example independently a fused ring of two or more, for example, a fused ring of three or more.

The $Ar^1$ and $Ar^2$ may independently be one of a phenyl group, a naphthyl group, an anthracenyl group, a tetracenyl group, a pentacenyl group, a thiophenyl group, a selenophenyl group, a tellurophenyl group, a furanyl group, a pyrrolyl group, and a fused ring of two or more rings therefrom.

The $X^1$ may be, for example, one of sulfur (S), selenium (Se), tellurium (Te), and oxygen (O).

The $Y^1$ may be, for example, one of fluorine (F), chlorine (Cl), bromine (Br), and iodine (I).

The first compound may include a chalcogen-containing group and a sulfonate group at ortho-positions to provide the first intermediate effectively.

The first compound may be a compound represented by Chemical Formula 1a.

[Chemical Formula 1a]

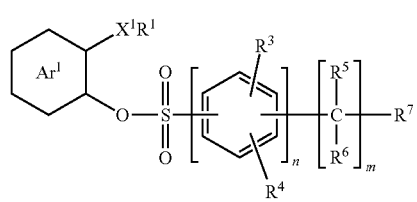

In Chemical Formula 1a, $Ar^1$ is one of a substituted or unsubstituted aromatic ring, a substituted or unsubstituted heteroaromatic ring, and a fused ring of two or more rings therefrom, $X^1$ is a chalcogen element, each of $R^1$ and $R^3$ to $R^7$ are independently one of hydrogen, a substituted or unsubstituted $C_1$ to $C_{20}$ alkyl group, a $C_1$ to $C_{20}$ fluoroalkyl group, a substituted or unsubstituted $C_6$ to $C_{20}$ aryl group, a halogen, and a combination thereof, n is 0, 1, or 2, and m is an integer of 0 to 10.

The first compound may be a compound represented by Chemical Formula 1aa.

[Chemical Formula 1aa]

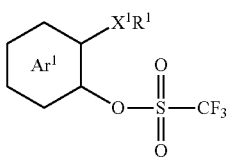

In Chemical Formula 1aa, $Ar^1$, $X^1$, and $R^1$ are the same as described above.

The second compound may be, for example represented by Chemical Formula 2a.

[Chemical Formula 2a]

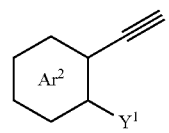

In Chemical Formula 2a, $Ar^2$ is independently one of a substituted or unsubstituted aromatic ring, a substituted or unsubstituted heteroaromatic ring, and a fused ring of two or more rings therefrom, and $Y^1$ is a halogen.

The second compound may be, for example represented by Chemical Formula 2aa.

[Chemical Formula 2aa]

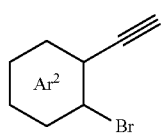

In Chemical Formula 2aa, $Ar^2$ is independently one of a substituted or unsubstituted aromatic ring, a substituted or unsubstituted heteroaromatic ring, and a fused ring of two or more rings therefrom.

The first compound and the second compound may be, for example, provided in a mole ratio of about 1:9 to 9:1, in a mole ratio of about 2:8 to 8:2, in a mole ratio of about 3:7 to 7:3, in a mole ratio of about 4:6 to 6:4, or in a mole ratio of about 5:5.

In the process of reacting the first compound with the second compound, a halogen salt may be provided, and the halogen salt may be, for example, potassium iodide, but is not limited thereto. The halogen salt may help eliminate a sulfonate group from the first compound, and thus, may promote a reaction.

In the process of reacting the first compound with the second compound, at least one catalyst may be provided, and for example the catalyst may be a metal catalyst, for example, a copper catalyst, e.g., copper iodide and/or a palladium catalyst, e.g., palladium (0) bis(triphenylphosphine)dichloride(bis(triphenylphosphine)dichloride), but is not limited thereto.

In the process of reacting the first compound with the second compound, a base compound may be provided, for example an amine, an amine derivative and/or a cesium carbonate. The amine derivative may be a primary amine, a secondary amine, and/or a tertiary amine, for example, trimethylamine, but is not limited thereto.

The process of reacting the first compound with the second compound may be performed in a solvent, and the solvent may be, for example, at least one selected from an aliphatic hydrocarbon solvent, e.g., hexane and heptane; an aromatic hydrocarbon solvent, e.g., toluene, pyridine, quinoline, anisole, mesitylene, and xylene; a ketone-based solvent, e.g., methyl isobutyl ketone, 1-methyl-2-pyrrolidinone (NMP), cyclohexanone, and acetone; an ether-based solvent, e.g., tetrahydrofuran and isopropyl ether; an acetate-based solvent, e.g., ethyl acetate, butyl acetate, and propylene glycol methyl ether acetate; an amide-based solvent, e.g., dimethyl acetamide and dimethyl formamide (DMF); a nitrile-based solvent, e.g., acetonitrile and benzonitrile; and a mixture of the solvents, but is not limited thereto.

The first intermediate obtained by reacting the first compound with the second compound may be an asymmetric ethylene derivative or asymmetric acetylene derivative and may be, for example, represented by Chemical Formula 3.

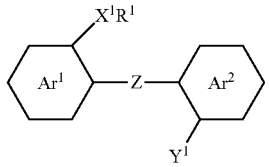

[Chemical Formula 3]

In Chemical Formula 3, each of $Ar^1$ and $Ar^2$ are independently one of a substituted or unsubstituted aromatic ring, a substituted or unsubstituted heteroaromatic ring, and a fused ring of two or more rings therefrom, $X^1$ is a chalcogen element, $R^1$ is independently one of hydrogen, a substituted or unsubstituted $C_1$ to $C_{20}$ alkyl group, a $C_1$ to $C_{20}$ fluoroalkyl group, a substituted or unsubstituted $C_6$ to $C_{20}$ aryl group, a halogen, and a combination thereof, Z is one of an ethene group and an ethyne group, and $Y^1$ is a halogen.

The $Ar^1$ and $Ar^2$ of Chemical Formula 3 may independently be, for example one of a phenyl group, a naphthyl group, an anthracenyl group, a tetracenyl group, a pentacenyl group, a thiophenyl group, a selenophenyl group, a tellurophenyl group, a furanyl group, a pyrrolyl group, and a fused ring of two or more rings therefrom.

The first intermediate may be, for example represented by Chemical Formula 3a.

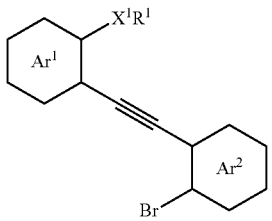

[Chemical Formula 3a]

In Chemical Formula 3a, each of $Ar^1$ and $Ar^2$ are independently one of a substituted or unsubstituted aromatic ring, a substituted or unsubstituted heteroaromatic ring, and a fused ring of two or more rings therefrom, for example one of a phenyl group, a naphthyl group, an anthracenyl group, a tetracenyl group, a pentacenyl group, a thiophenyl group, a selenophenyl group, a tellurophenyl group, a furanyl group, a pyrrolyl group, and a fused ring of two or more rings therefrom, $X^1$ is a chalcogen element, and $R^1$ is one of hydrogen, a substituted or unsubstituted $C_1$ to $C_{20}$ alkyl group, a $C_1$ to $C_{20}$ fluoroalkyl group, a substituted or unsubstituted $C_6$ to $C_{20}$ aryl group, a halogen, and a combination thereof.

The process of obtaining the second intermediate may include providing a halogen molecule with the first intermediate. The halogen molecule may be, for example an iodine molecule ($I_2$), but is not limited thereto.

The process of obtaining the second intermediate may be performed in a solvent, and the solvent may be, for example at least one selected from an aliphatic hydrocarbon solvent such as hexane and heptane; an aromatic hydrocarbon solvent such as toluene, pyridine, quinoline, anisole, mesitylene, and xylene; a ketone-based solvent such as methyl isobutyl ketone, 1-methyl-2-pyrrolidinone (NMP), cyclohexanone, and acetone; t an ether-based solvent such as tetrahydrofuran and isopropyl ether; ethyl acetate, butyl acetate, propylene glycol methyl ether acetate and the like acetate based solvent; an acetate-based solvent such as ethyl acetate, butyl acetate, and propylene glycol methyl ether acetate; an amide-based solvent such as dimethyl acetamide and dimethyl formamide (DMF); a nitrile-based solvent such as acetonitrile and benzonitrile; and a mixture of the solvents, but is not limited thereto.

In the process of obtaining the second intermediate, a ring including a chalcogen element may be formed by a ring closure reaction of the first intermediate, and for example the second intermediate may include one of a thiophene ring, a selenophene ring, a tellurophene ring and a furan ring.

The second intermediate may be, for example, represented by Chemical Formula 4.

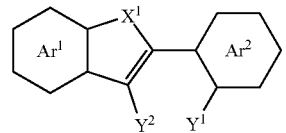

[Chemical Formula 4]

In Chemical Formula 4, each of $Ar^1$ and $Ar^2$ are independently one of a substituted or unsubstituted aromatic ring, a substituted or unsubstituted heteroaromatic ring, and a fused ring of two or more rings therefrom, $X^1$ is a chalcogen element, and each of $Y^1$ and $Y^2$ are independently a halogen.

The $Ar^1$ and $Ar^2$ of Chemical Formula 4 may independently be one of a phenyl group, a naphthyl group, an anthracenyl group, a tetracenyl group, a pentacenyl group, a thiophenyl group, a selenophenyl group, a tellurophenyl group, a furanyl group, a pyrrolyl group, and a fused ring of two or more rings therefrom.

The second intermediate may be, for example, represented by Chemical Formula 4a.

[Chemical Formula 4a]

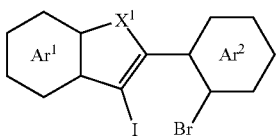

In Chemical Formula 4a, each of Ar$^1$ and Ar$^2$ are independently one of a substituted or unsubstituted aromatic ring, a substituted or unsubstituted heteroaromatic ring, and a fused ring of two or more rings therefrom, for example one of a phenyl group, a naphthyl group, an anthracenyl group, a tetracenyl group, a pentacenyl group, a thiophenyl group, a selenophenyl group, a tellurophenyl group, a furanyl group, a pyrrolyl group, and a fused ring of two or more rings therefrom, and X$^1$ may be a chalcogen element.

The second intermediate may be produced as a fused heteroaromatic compound having chalcogen elements by providing a chalcogen element and catalytic cyclization reaction.

The chalcogen element may be the same as or different from the chalcogen element of the first compound, and may be, for example, one of sulfur (S), selenium (Se), tellurium (Te), and oxygen (O).

In the process of obtaining the fused heteroaromatic compound, for example, a copper reagent (e.g., copper iodide and/or Cu(OTf) (copper trifluoromethanesulfonate), a palladium reagent (e.g., Pd(PPh$_3$)$_4$, and/or Pd$_2$(dba)$_3$ (tris(dibenzylideneacetone)dipalladium (0)) and/or a catalyst combined with a phosphine ligand (e.g., 1,1'-bis(diphenylphosphino)ferrocene (dppf) or bis[2-(diphenylphosphino)phenyl]ether (DPEPhos), may be provided but is not limited thereto.

In the process of obtaining the fused heteroaromatic compound, for example an inorganic base (e.g., potassium carbonate (K$_2$CO$_3$) or an organic base (e.g., triisopropylamine) may be provided, but is not limited thereto.

The process of obtaining the fused heteroaromatic compound may be performed in a solvent, and the solvent may be, for example, at least one selected from an aliphatic hydrocarbon solvent (e.g., hexane and heptane); an aromatic hydrocarbon solvent (e.g., toluene, pyridine, quinoline, anisole, mesitylene, and xylene); a ketone-based solvent (e.g., methyl isobutyl ketone, 1-methyl-2-pyrrolidinone (NMP), cyclohexanone, and acetone); an ether-based solvent (e.g., tetrahydrofuran and isopropyl ether); an acetate-based solvent (e.g., ethyl acetate, butyl acetate, and propylene glycol methyl ether acetate); an amide-based solvent (e.g., dimethyl acetamide and dimethyl formamide (DMF)); a nitrile-based solvent (e.g., acetonitrile and benzonitrile); and a mixture of the solvents, but is not limited thereto.

The fused heteroaromatic compound may be, for example, represented by Chemical Formula 5.

[Chemical Formula 5]

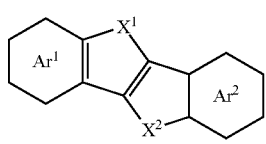

In Chemical Formula 5, each of Ar$^1$ and Ar$^2$ are independently one of a substituted or unsubstituted aromatic ring, a substituted or unsubstituted heteroaromatic ring, and a fused ring of two or more rings therefrom, and each of X$^1$ and X$^2$ may independently be a chalcogen element.

For example, the fused heteroaromatic compound may be represented by one of Chemical Formulae 5a to 5f, but is not limited thereto.

[Chemical Formula 5a]

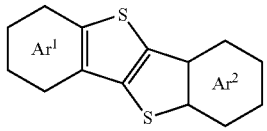

[Chemical Formula 5b]

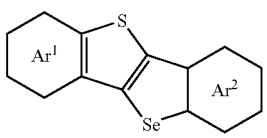

[Chemical Formula 5c]

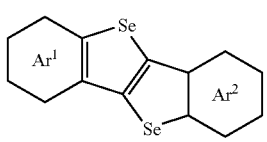

[Chemical Formula 5d]

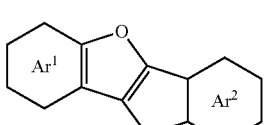

[Chemical Formula 5e]

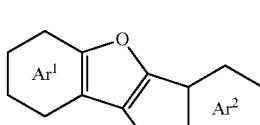

[Chemical Formula 5f]

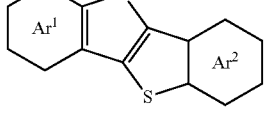

In Chemical Formulae 5a to 5f, each of Ar$^1$ and Ar$^2$ are independently one of a substituted or unsubstituted aromatic ring, a substituted or unsubstituted heteroaromatic ring, and a fused ring of two or more rings therefrom, for example one of a phenyl group, a naphthyl group, an anthracenyl group, a tetracenyl group, a pentacenyl group, a thiophenyl group, a selenophenyl group, a tellurophenyl group, a furanyl group, a pyrrolyl group, and a fused ring of two or more rings therefrom.

The fused heteroaromatic compound has, for example, a structure where four or more aromatic rings and/or heteroaromatic rings are fused, and has a uniform and stable oxidation potential when applied to an electronic device (e.g., an organic thin film transistor) due to a compact planar molecular structure, and shows relatively high charge mobility because the intermolecular packing and stacking are improved. Therefore, the fused heteroaromatic compound may be effectively used as a charge transporting material (e.g., a semiconductor).

The fused heteroaromatic compound may have, for example a structure where five or more aromatic rings and/or heteroaromatic rings are fused, six or more aromatic rings and/or heteroaromatic rings are fused, seven or more aromatic rings and/or heteroaromatic rings are fused, or eight or more aromatic rings and/or heteroaromatic rings are fused.

The fused heteroaromatic compound may have, for example, a molecular weight of about 300 to about 3,000, or about 300 to about 1,500.

The fused heteroaromatic compound may be, for example, a compound represented by one of Chemical Formulae (1) to (16), but is not limited thereto.
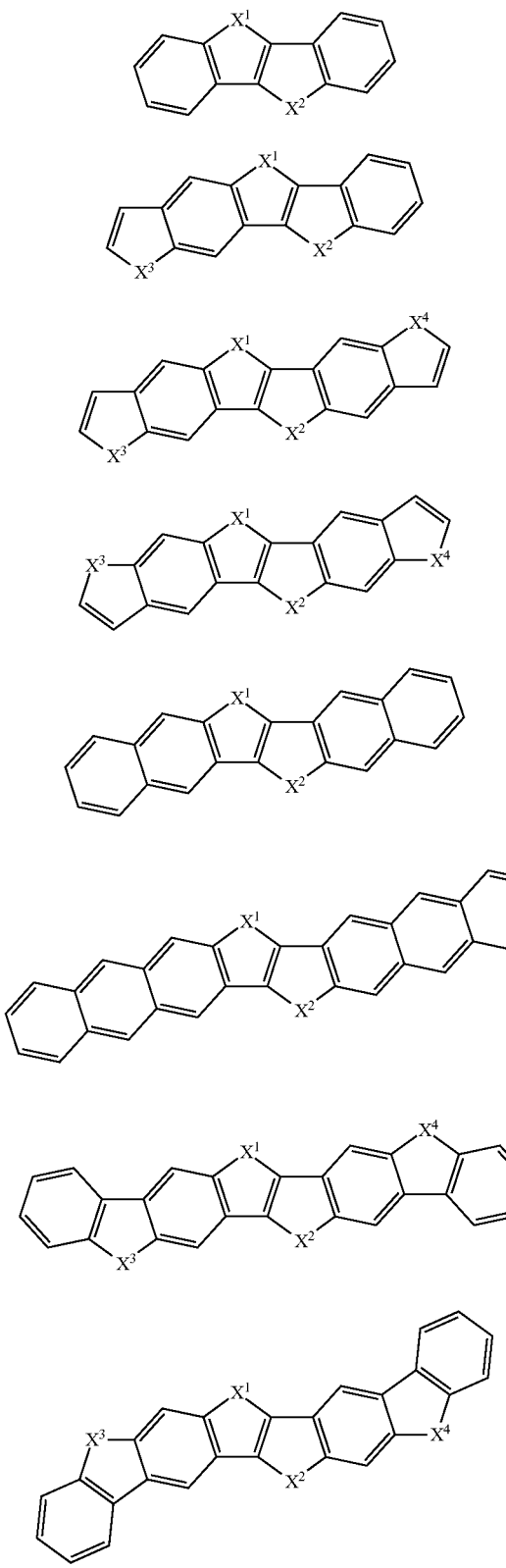
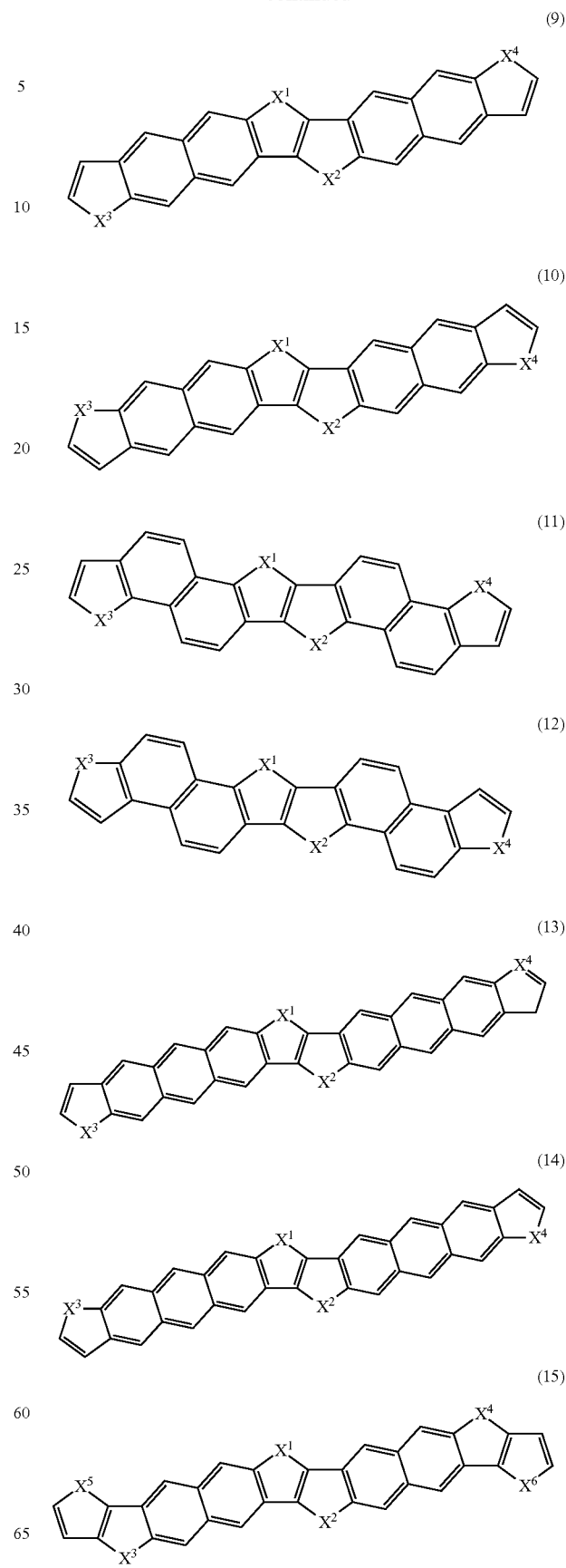

-continued

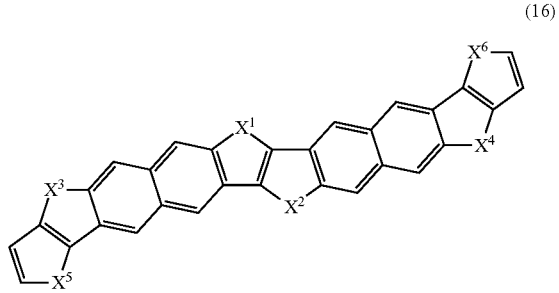
(16)

In Chemical Formulae (1) to (16), each of $X^1$ and $X^2$ are independently one of sulfur (S), selenium (Se), tellurium (Te), and oxygen (O), each of $X^3$ to $X^6$ are independently one of sulfur (S), selenium (Se), tellurium (Te), oxygen (O), and $NR^7$, wherein $R^7$ is hydrogen, a $C_1$ to $C_{10}$ alkyl group, or a $C_6$ to $C_{30}$ aryl group.

In Chemical Formulae (1) to (16), each aromatic ring and/or heteroaromatic ring may be, for example substituted with at least one substituent, for example, a $C_1$ to $C_{10}$ alkyl group or a $C_6$ to $C_{30}$ aryl group.

The fused heteroaromatic compound may be, for example, one of the compounds of Group 1, but is not limited thereto.

[Group 1]

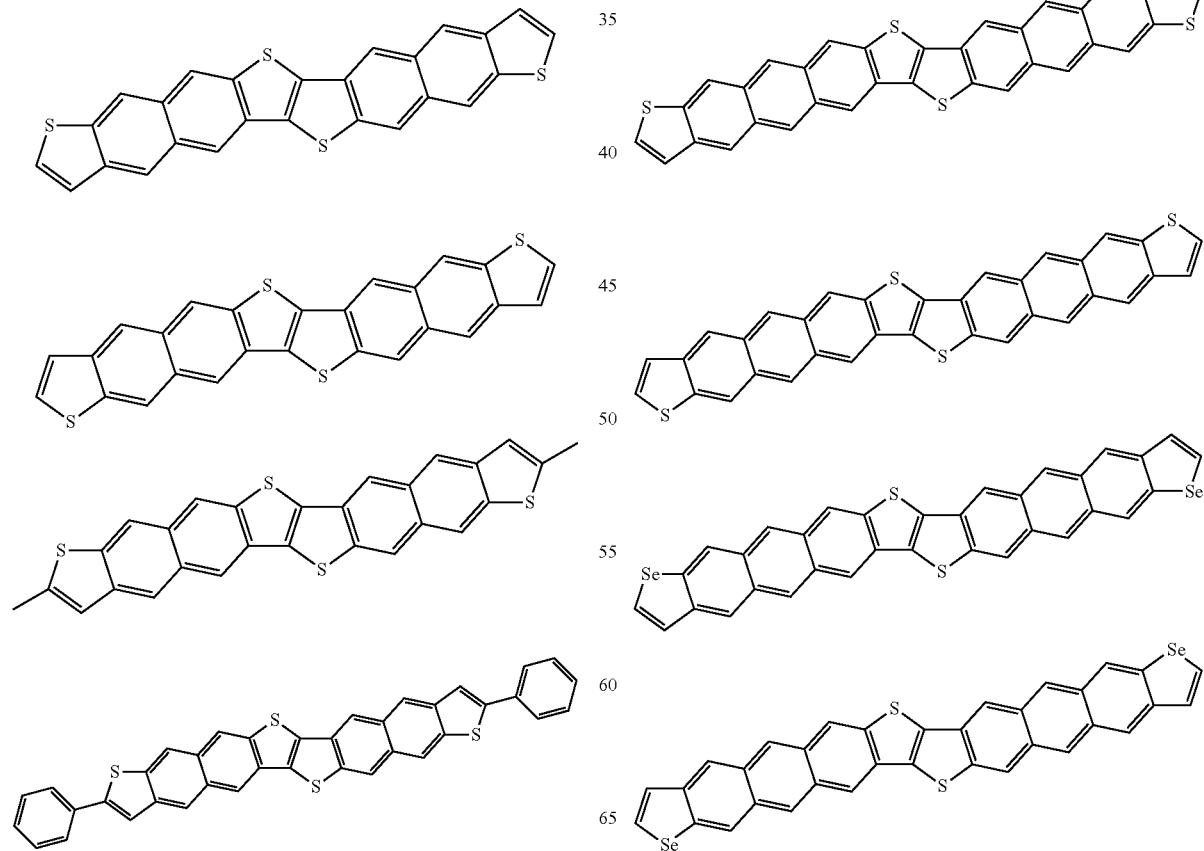

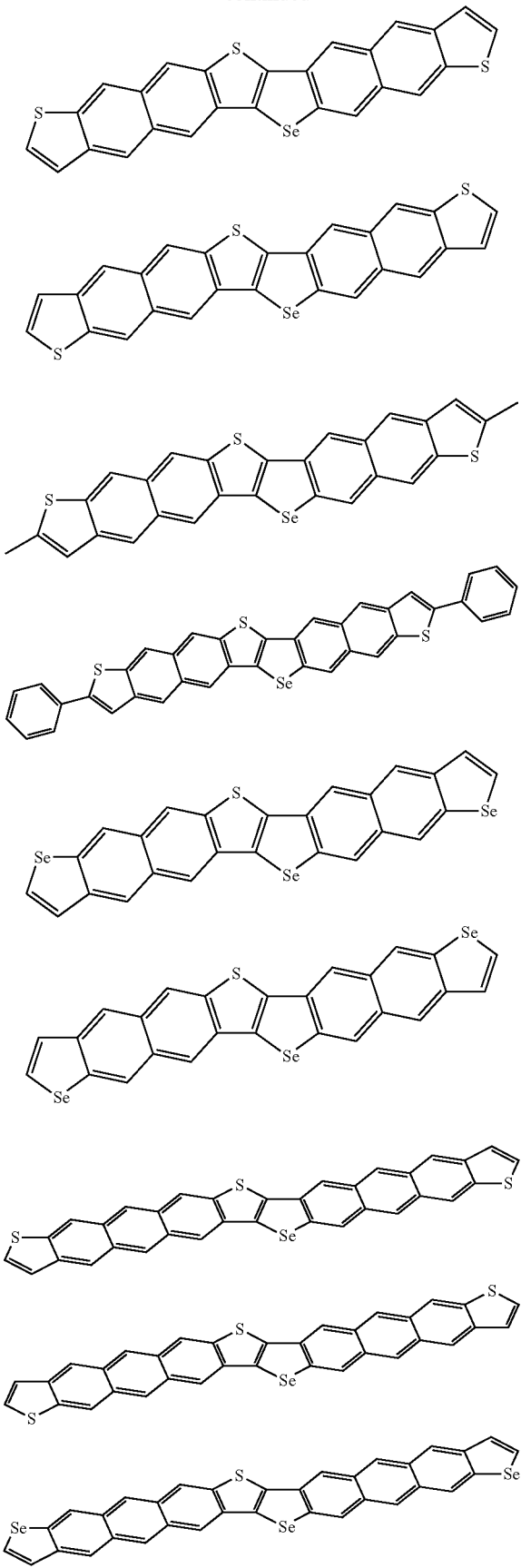
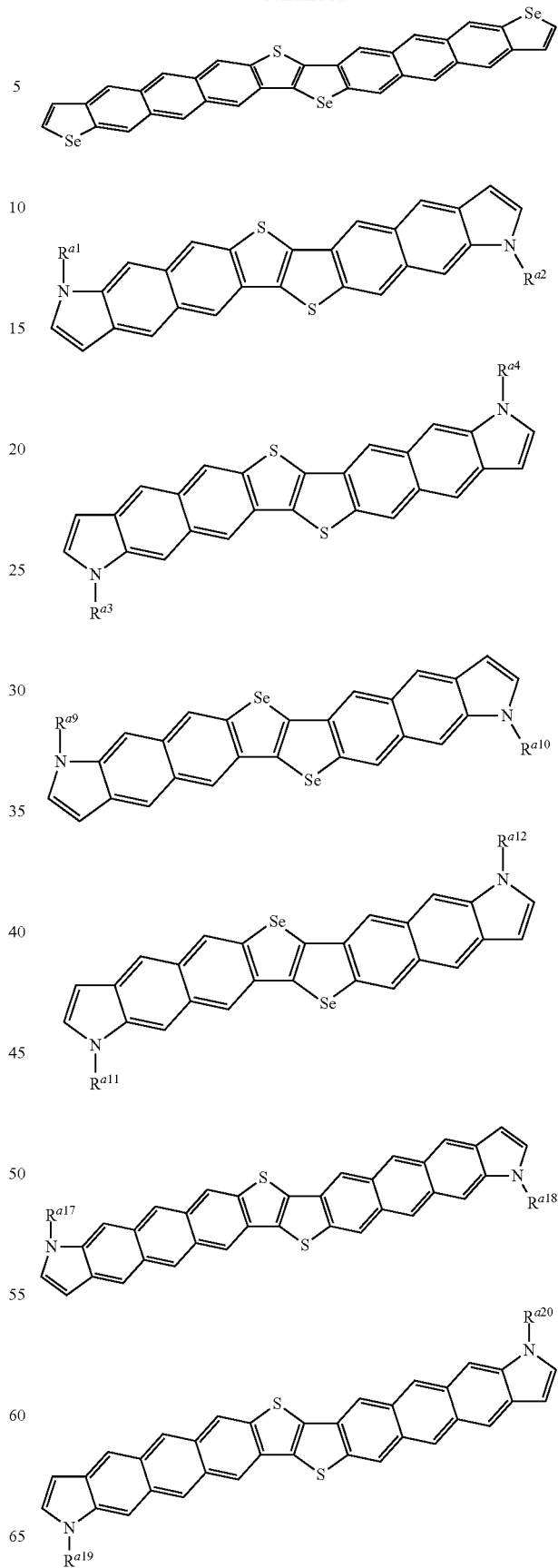

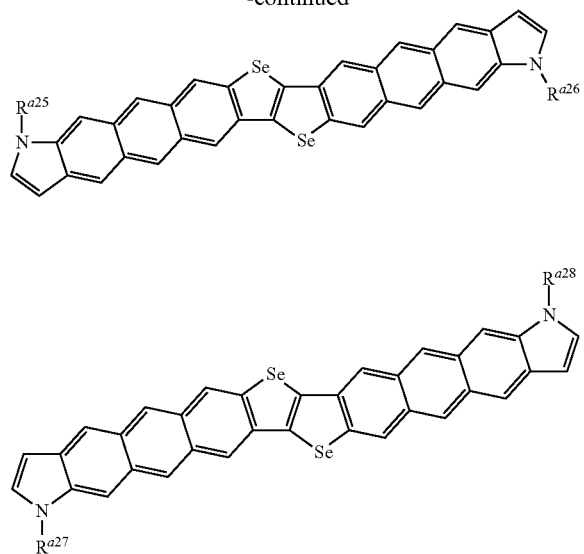

In Group 1, each of $R^{a1}$ to $R^{a4}$, $R^{a9}$ to $R^{a12}$, $R^{a17}$ to $R^{a20}$, and $R^{a25}$ to $R^{a28}$ are independently one of hydrogen, a substituted or unsubstituted $C_1$ to $C_{10}$ alkyl group, and a substituted or unsubstituted $C_6$ to $C_{30}$ aryl group.

The method of synthesizing a fused heteroaromatic compound may be relatively simple, and may provide a product with a relatively high yield. The synthetic method may be performed at a relatively low temperature of, for example about 40° C. to about 200° C., for example, about 40° C. to about 100° C. The synthetic method may be performed in a relatively short time, and may shorten a time of a conventional method by a half or more. The synthetic method may provide intermediates and a final product with a relatively high yield, and for example each intermediate and final product may be produced with a yield of about 70% or more, for example, about 80% or more.

The fused heteroaromatic compound may be implemented into an organic thin film by a deposition or solution process. The organic thin film may be applied to various devices including an organic semiconductor. For example, the fused heteroaromatic compound may be applied to an organic thin film transistor, and may be applied to a charge transport layer and/or an active layer of an electronic device (e.g., a solar cell, an organic light emitting diode (OLED) display, and an organic sensor).

Hereinafter, one example of an organic thin film transistor including the fused heteroaromatic compound is described referring to the drawing.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

The FIGURE is a cross-sectional view of an organic thin film transistor according to example embodiments.

A gate electrode 124 is formed on a substrate 110 made of transparent glass, silicon, or plastic. The gate electrode 124 is connected to a gate line (not shown) transferring a gate signal. The gate electrode 124 may be made of gold (Au), copper (Cu), nickel (Ni), aluminum (Al), molybdenum (Mo), chromium (Cr), tantalum (Ta), titanium (Ti), an alloy thereof, or a combination thereof.

A gate insulating layer 140 is formed on the gate electrode 124. The gate insulating layer 140 may be made of an organic material or an inorganic material. Examples of the organic material may include a soluble polymer compound (e.g., a polyvinyl alcohol-based compound, a polyimide-based compound, a polyacryl-based compound, a polystyrene-based compound, and benzocyclobutane (BCB)), and examples of the inorganic material may include a silicon nitride ($SiN_x$) and a silicon oxide ($SiO_2$).

A source electrode 173 and a drain electrode 175 are formed on the gate insulating layer 140. The source electrode 173 and the drain electrode 175 face each other with the gate electrode 124 therebetween. The source electrode 173 is electrically connected to the data line (not shown) transferring the data signal. The source electrode 173 and the drain electrode 175 may include at least one metal selected from gold (Au), copper (Cu), nickel (Ni), aluminum (Al), molybdenum (Mo), chromium (Cr), tantalum (Ta), titanium (Ti), an alloy thereof, or a combination thereof.

An organic semiconductor 154 is formed on the source electrode 173 and the drain electrode 175. The organic semiconductor 154 may include the fused heteroaromatic compound. The organic semiconductor 154 may be formed in a solution process such as spin coating, slit coating, or inkjet printing by preparing the fused heteroaromatic compound as a solution. However, the fused heteroaromatic compound may be formed using a dry process (e.g., deposition).

Although the bottom gate structured organic thin film transistor is illustrated as an organic thin film transistor, it is not limited thereto, and it may be applied to all organic thin film transistors, e.g., a top gate structured organic thin film transistor.

The organic thin film transistor may be applied to a switching or driving device of various electronic devices, and the electronic device may be, for example, a liquid crystal display (LCD), an organic light emitting diode (OLED) display, an electrophoretic display device, or an organic sensor.

Hereinafter, the present disclosure is illustrated in more detail with reference to examples. However, these are examples, and the present disclosure is not limited thereto.

Synthesis of Fused Heteroaromatic Compound

Synthesis Example 1

[Reaction Scheme 1]
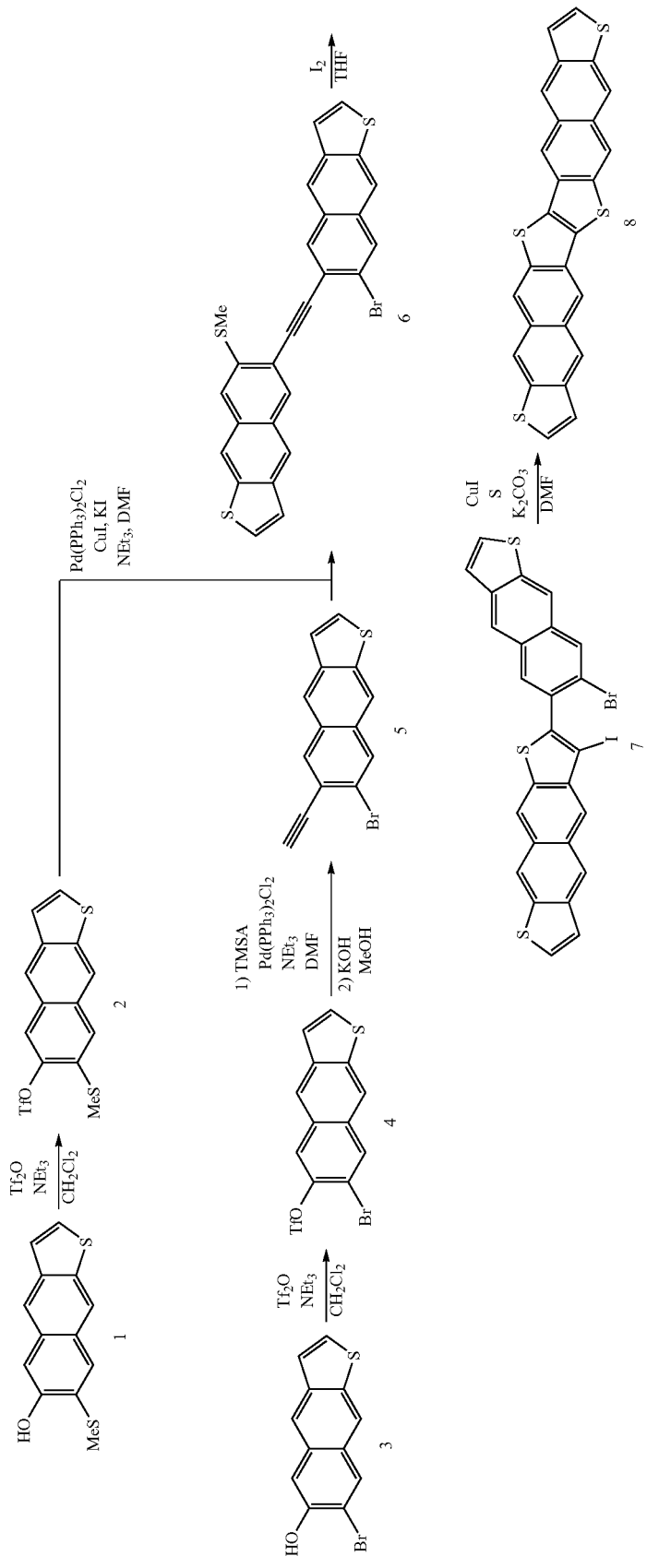

Synthesis of Compound 2:

10.0 g (40.6 mmol) of the compound 1 is put in a flask and dissolved in 500 mL of dichloromethane ($CH_2Cl_2$). Subsequently, 15 mL (0.11 mol) triethylamine ($NEt_3$) is added thereto, 8.9 mL (53 mmol) of trifluoromethansulfonic anhydride ($Tf_2O$) is added thereto at 0° C., and the obtained mixture is additionally stirred overnight. Then, a saturated ammonium chloride solution and water are added thereto. Subsequently, a water layer is separated and the extraction is performed with dichloromethane. Then, an organic layer therefrom is washed with a saturated saline solution, dried and concentrated with anhydrous magnesium sulfate, and purified through column chromatography to obtain 15 g of a compound 2.

NMR ($CDCl_3$, 300 MHz) 7.43 (d, 1H, J=5.7 Hz), 7.57 (d, 1H, J=5.7 Hz), 7.73 (s, 1H), 7.86 (s, 1H), 8.29 (s, 1H), 8.32 (s, 1H).

MS (EI-MS, m/z) 378 (M+)

Synthesis of Compound 4:

5.0 g (15 mmol) of the compound 3 is put in a flask and dissolved in 250 mL of dichloromethane ($CH_2Cl_2$). Subsequently, 6.0 mL (0.042 mol) of triethylamine ($NEt_3$) is added thereto, 3.4 mL (20 mmol) of trifluoromethansulfonic anhydride ($Tf_2O$) is added thereto at 0° C., and the obtained mixture is additionally stirred overnight. Then, a saturated ammonium chloride solution and water are added thereto. Subsequently, a water layer is separated and the extraction is performed with dichloromethane. Subsequently, an organic layer therefrom is washed with a saturated saline solution, dried and concentrated with anhydrous magnesium sulfate, and purified through column chromatography to obtain 6.6 g of a compound 4. The yield of the compound is 94%.

NMR ($CDCl_3$, 300 MHz) 7.45 (d, 1H, J=5.7 Hz), 7.63 (d, 1H, J=5.7 Hz), 7.95 (s, 1H), 8.26 (s, 1H), 8.34 (s, 1H), 8.34 (s, 1H).

MS (EI-MS, m/z) 412 (M+)

Synthesis of Compound 5:

6.0 g (13 mmol) of the compound 4, 60 mL of dimethyl formamide (DMF), and 11 mL (0.080 mol) of triethylamine ($NEt_3$) are put in a flask. Subsequently, 2.0 mL (14 mmol) of trimethylsilylacetylene (TMSA), 74 mg (0.39 mmol) of copper iodide, palladium bis(triphenylphosphine)dichloride, and 270 mg (0.39 mmol) of $Pd(PPh_3)_2Cl_2$) are added thereto, and the mixture is stirred overnight. Then, a saturated ammonium chloride solution and water are added thereto, and a water layer is extracted with dichloromethane. Subsequently, an organic layer therefrom is washed with a saline solution, dried with anhydrous magnesium sulfate, and purified through column chromatography to obtain a crude product. The crude product is suspended in 250 mL of methanol (MeOH), 1.3 g (24 mmol) of potassium hydroxide (KOH) is added thereto. Subsequently, the mixture is stirred for 4 hours, and water is added thereto to precipitate 3.2 g of a solid compound 5. The yield of the compound is 94%.

NMR ($CDCl_3$, 300 MHz) 7.43 (d, 1H, J=5.7 Hz), 7.57 (d, 1H, J=5.7 Hz), 8.17 (s, 1H), 8.22 (s, 1H), 8.25 (s, 1H), 8.26 (s, 1H).

MS (EI-MS, m/z) 286 (M+)

Synthesis of Compound 6 (First Intermediate):

2.0 g (5.2 mmol) of the compound 2, 128 mg (0.78 mmol) of copper iodide (CuI), 92 mg (0.13 mmol) of palladium (0) bis(triphenylphosphine)dichloride ($Pd(PPh_3)_2Cl_2$), 1.3 g (7.8 mmol) of potassium iodide (KI), 6 mL of triethylamine ($NEt_3$), and 30 mL of dimethyl formamide (DMF) are put in a flask and stirred for 15 minutes. Subsequently, 1.5 g (5.2 mmol) of the compound 5 is added thereto, the obtained mixture is stirred at 70° C. overnight to precipitate 2.6 g of a solid compound 6. The yield of the compound is 96%.

NMR ($CDCl_3$, 300 MHz) 2.69 (s, 3H), 7.42-7.58 (m, 5H), 8.20 (s, 1H), 8.28-8.31 (m, 5H), 8.35 (s, 1H).

MS (LC-TOF-MS, m/z) 515.61 (M+)

Synthesis of Compound 7 (Second Intermediate):

2.6 g (5.0 mmol) of the compound 6 and 400 mL of tetrahydrofuran (THF) are put in a flask. Subsequently, 2.5 g (10 mmol) of iodine (I2) is added thereto, and the mixture is stirred overnight. Then, methanol is added thereto, and a precipitate therefrom is filtered to obtain 2.7 g of a compound 7. The yield of the compound is 87%.

NMR ($CDCl_3$, 300 MHz) 7.46-7.49 (m, 2H), 7.54 (d, 1H, J=5.4 Hz), 7.60 (d, 1H, J=5.7 Hz), 8.11 (s, 1H), 8.33 (s, 1H), 8.37 (s, 1H), 8.39 (s, 1H), 8.41 (s, 1H), 8.49 (s, 1H), 8.50 (s, 1H), 8.60 (s, 1H).

MS (MALDI-TOF-MS, m/z) 625.69 (M+)

Synthesis of Compound 8 (Final Compound):

2.7 g (4.4 mmol) of the compound 7, 165 mg (0.87 mmol) of copper iodide (CuI), 0.42 g (13 mmol) of sulfur powder (S), and potassium 1.8 g (13 mmol) of carbonate ($K_2CO_3$) are put in a flask. Subsequently, 250 mL of dimethyl formamide (DMF) is added thereto, and the mixture is stirred at 110° C. overnight. Then, the resultant is cooled down to 0° C. to obtain a crude product as a precipitate. The crude product is suspended in a mixed solvent of dimethyl acetamide and water, filtered, and washed with water, acetone, and tetrahydrofuran (THF) to obtain 1.8 g of a compound 8. The yield of the compound is 90%.

MS (MALDI-TOF-MS, m/z) 452.04 (M+)

Synthesis Example 2

[Reaction Scheme 2]
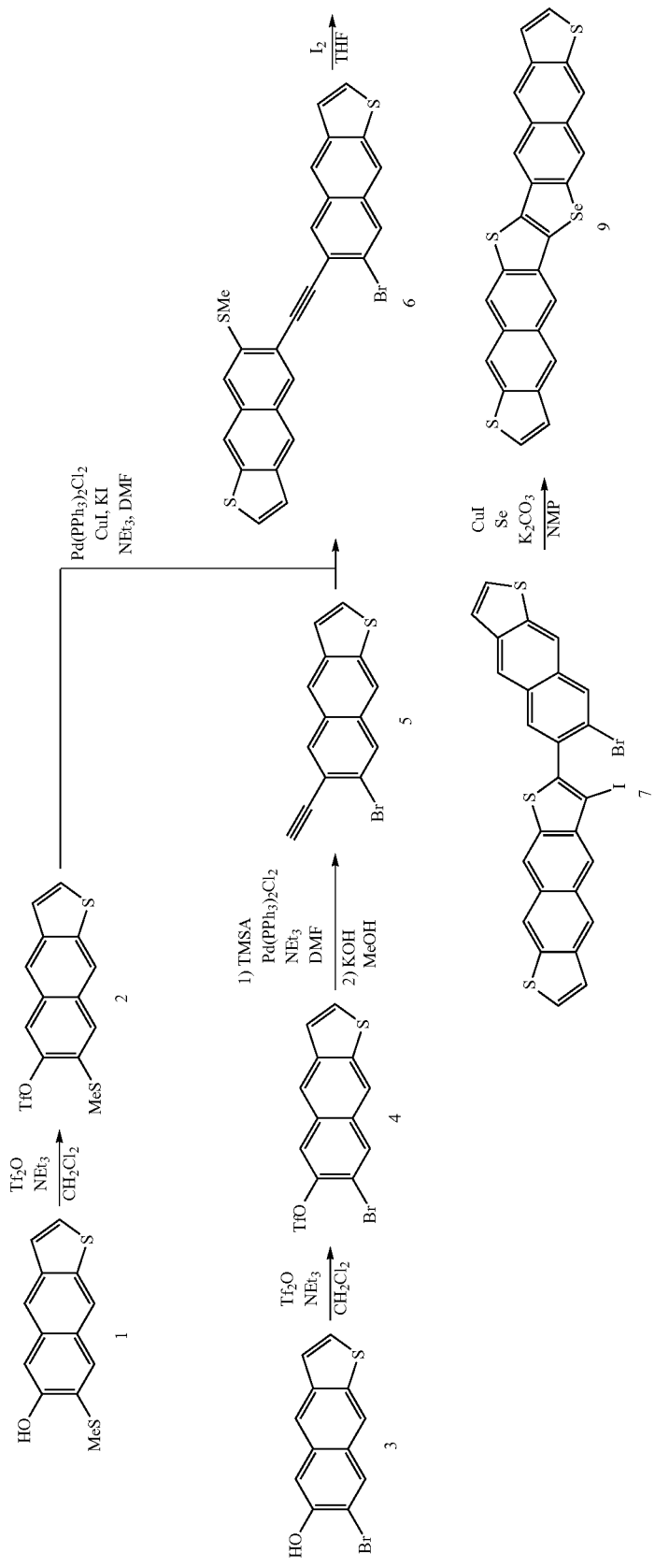

Synthesis of Compounds 2, 4, 5, 6, and 7:
The compounds 2, 4, 5, 6, and 7 are respectively synthesized according to the same method as Synthesis Example 1.

Synthesis of Compound 9 (Final Compound):
20 mg (0.032 mmol) of the compound 7, 0.9 mg (0.006 mmol) of copper iodide (CuI), 7.6 mg (0.0096 mmol) of selenium powder (Se), and 13 mg (0.0096 mmol) of potassium carbonate ($K_2CO_3$) are put in a flask, 2 mL of N-methylpyrrolidone (NMP) is added thereto, and the mixture is stirred at 120° C. overnight. Subsequently, the resultant is cooled down to 0° C. to precipitate a solid. The precipitated solid is suspended in a mixed solvent of dimethyl acetamide and water, filtered, and washed with water, acetone, and tetrahydrofuran (THF) to obtain 12 mg of a compound 9. The yield of the compound is 75%.

MS (MALDI-TOF-MS, m/z) 500.02 (M+)

Synthesis Example 3

[Reaction Scheme 3]

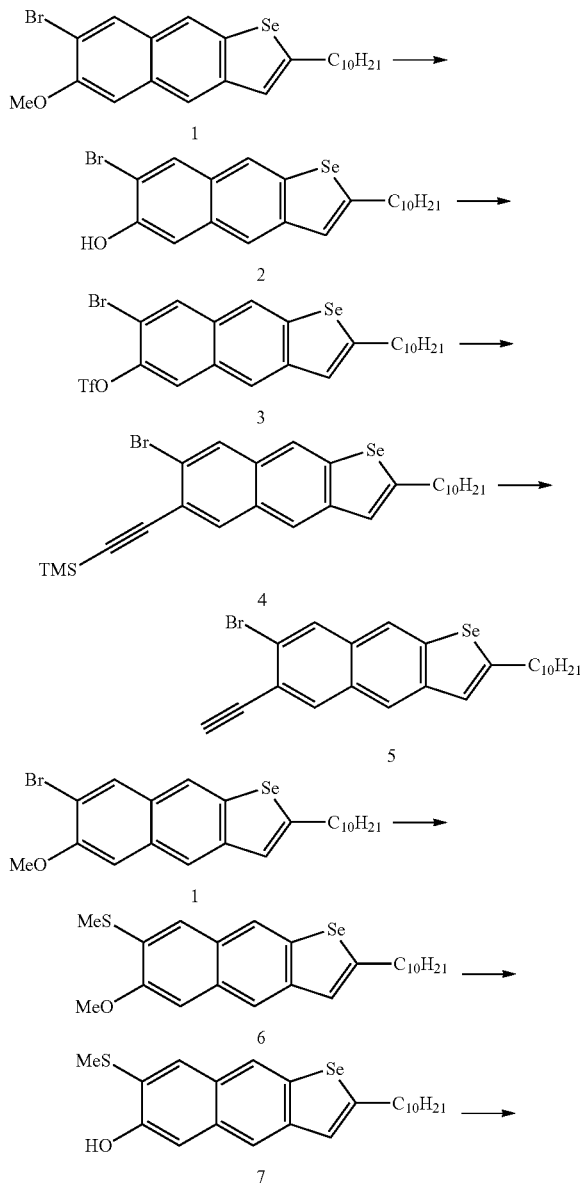

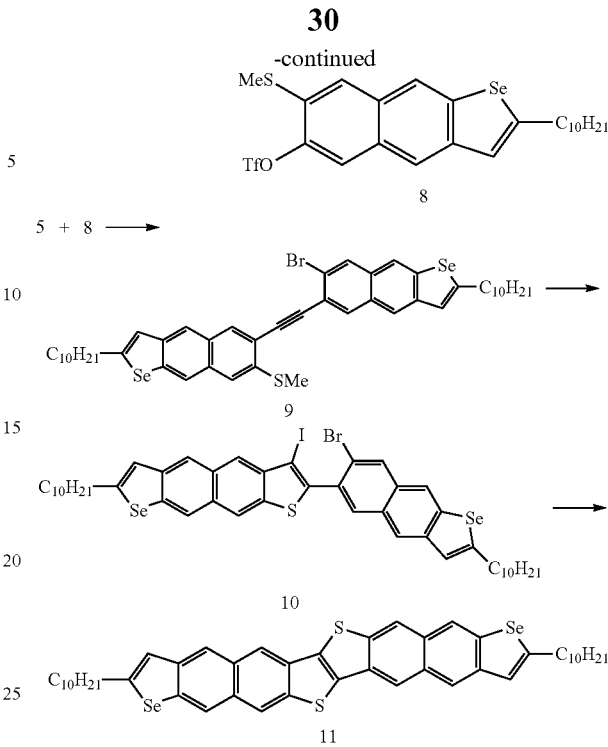

Synthesis of Compound 2:
2.0 g (4.2 mmol) of the compound 1 is put in a flask and dissolved in 200 mL of dichloromethane ($CH_2Cl_2$). Subsequently, after cooling, 4.2 mL (4.2 mmol) of 1M tribromoboron ($BBr_3$) solution is added thereto, and the obtained mixture is additionally stirred for 4 hours. Then, a saturated ammonium chloride solution is added thereto and then the extraction is performed with chloroform. Then, the resultant is dried with anhydrous magnesium sulfate, filtered and removed remaining solvent to obtain a compound 2 of yellow solid. The yield is 99%.

NMR($CDCl_3$, 300 MHz) 0.88 (t, 3H), 1.27 (m, 14H), 1.75 (m, 2H), 2.94 (t, 2H), 5.55 (s, 1H), 7.18 (s, 1H), 7.44 (s, 1H), 7.96 (s, 1H), 8.01 (s, 1H), 8.10 (s, 1H).

Synthesis of Compound 3:
1.8 g (3.9 mmol) of the compound 2 is put in a flask and dissolved in 90 mL of dichloromethane ($CH_2Cl_2$). Subsequently, 1.5 mL (10.5 mmol) of triethylamine ($NEt_3$) is added thereto, 0.86 mL (5.1 mmol) of trifluoromethansulfonic anhydride ($Tf_2O$) is added thereto at 0° C., and the obtained mixture is additionally stirred overnight. Then, a saturated ammonium chloride solution and water are added thereto. Subsequently, a water layer is separated and the extraction is performed with dichloromethane. Subsequently, an organic layer therefrom is washed with a saturated saline solution, dried and concentrated with anhydrous magnesium sulfate, and purified through column chromatography to obtain a compound 3. The yield of the compound 3 is 100%.

NMR ($CDCl_3$, 300 MHz) 0.89 (t, 3H), 1.27 (m, 14H), 1.76 (m, 2H), 2.97 (t, 2H), 7.25 (s, 1H), 7.86 (s, 1H), 8.09 (s, 1H), 8.15 (s, 1H), 8.21 (s, 1H).

Synthesis of Compounds 4 and 5:
2.3 g (3.8 mmol) of the compound 3, 50 mL of dimethyl formamide (DMF), and 3.2 mL (23 mmol) of triethylamine ($NEt_3$) are put in a flask. Subsequently, 0.54 mL (3.8 mmol) of trimethylsilylacetylene (TMSA), 21 mg (0.11 mmol) of copper iodide, 77 mg (0.11 mmol) of palladium bis(triphenylphosphine)dichloride Pd(PPh$_3$)$_2$Cl$_2$ are added thereto, and the mixture is stirred overnight. Then, a saturated ammonium chloride solution and water are added thereto, and a water layer is extracted with dichloromethane. Subsequently, an organic layer therefrom is washed with a saline solution, dried with anhydrous magnesium sulfate, and purified through column chromatography to obtain a crude product. The crude product is suspended in 100 mL of methanol (MeOH), 0.83 g (14.8 mmol) of potassium hydroxide (KOH) is added thereto. Subsequently, the mixture is stirred for 4 hours, and water is added thereto to precipitate 3.2 g of a solid compound 5. The yield of the compound is 81%.

NMR (CDCl$_3$, 300 MHz) 0.87 (t, 3H), 1.27 (m, 14H), 1.75 (m, 2H), 2.95 (t, 2H), 3.40 (s, 1H), 7.23 (s, 1H), 8.02 (s, 1H), 8.07 (s, 1H), 8.14 (s, 1H), 8.16 (s, 1H).

Synthesis of Compound 6 (First Intermediate):

4.0 g (8.3 mmol) of the compound 1, 0.76 g (10.8 mmol) of sodium thiomethoxide (NaSMe), 1.5 g (10.8 mmol) of potassium carbonate (K$_2$CO$_3$), 0.76 g (0.8 mmol) of tris (dibenzylideneacetone)dipalladium(0), and 0.9 g (1.7 mmol) of bis[2-diphenylphosphino]phenyl]ether are put in a flask and added 200 ml of toluene, and then stirred for 24 hours at 110° C. After cooling, sodium hydrogen carbonate is added thereto, and the extraction is performed with toluene. Subsequently, the resultant is dried with anhydrous magnesium sulfate, filtered, and an organic solvent is removed under vacuum. Then, the resultant is purified through silica gel column chromatography (solvent: hexane and chloroform) to obtain a compound 6 of white solid. The yield of the compound 6 is 66%.

NMR (CDCl$_3$, 300 MHz) 0.88 (t, 3H), 1.27 (m, 14H), 1.75 (m, 2H), 2.55 (s, 3H), 2.94 (t, 2H), 4.01 (s, 3H), 7.12 (s, 1H), 7.18 (s, 1H), 7.44 (s, 1H), 7.97 (s, 1H), 8.11 (s, 1H).

Synthesis of Compound 7

3.1 g (6.9 mmol) of the compound 6 and 300 mL of dichloromethane are put in a flask. After cooling, 10.3 ml (10.3 mmol) of tribromoboron (BBr$_3$) solution is added thereto, and the mixture is stirred for 4 hours. Then, a saturated ammonium chloride solution is added thereto, and the extraction is performed with chloroform. Subsequently, an organic layer therefrom is dried with anhydrous magnesium sulfate, and filtered to obtain a compound 7 of yellow solid. The yield of the compound 7 is 99%.

NMR (CDCl$_3$, 300 MHz) 0.88 (t, 3H), 1.27 (m, 14H), 1.75 (m, 2H), 2.44 (s, 3H), 2.94 (t, 2H), 6.56 (s, 1H), 7.18 (s, 1H), 7.37 (s, 1H), 7.95 (s, 1H), 8.00 (s, 1H), 8.13 (s, 1H).

Synthesis of Compound 8

3.03 g (7.0 mmol) of the compound 7 and 300 ml of dichloromethane (CH$_2$Cl$_2$) are put in a flask and the mixture is stirred. Subsequently, 2.6 mL (18.9 mmol) of triethylamine is added thereto, and then 1.8 mL (10.5 mmol) of trifluoromethansulfonic anhydride (Tf$_2$O) is added thereto at 0° C., and the obtained mixture is additionally stirred overnight. Then, a saturated ammonium chloride solution and water are added thereto. Subsequently, a water layer is separated and the extraction is performed with dichloromethane. Subsequently, an organic layer therefrom is washed with a saturated saline solution, dried and concentrated with anhydrous magnesium sulfate, and purified through column chromatography to obtain a compound 8. The yield of the compound 8 is 93%.

NMR (CDCl$_3$, 300 MHz) 0.88 (t, 3H), 1.27 (m, 14H), 1.76 (m, 2H), 2.60 (s, 3H), 2.96 (t, 2H), 7.22 (s, 1H), 7.66 (s, 1H), 7.78 (s, 1H), 8.05 (s, 1H), 8.21 (s, 1H).

Synthesis of Compound 9 (First Intermediate)

3.67 g (6.5 mmol) of the compound 8, 50 mL of dimethyl formamide (DMF), 180 mg (0.98 mmol) of copper iodide, 140 mg (0.2 mmol) of palladium(0) bis(triphenylphosphine) dichloride Pd(PPh$_3$)$_2$Cl$_2$, 3.6 g (9.8 mmol) of tetrabutylammonium iodide Bu$_4$NI, and 10 ml of triethylamine (NEt$_3$) are put in a flask and the mixture is stirred for 15 minutes. Then, 3.08 g (6.5 mmol) of the compound 5 is added thereto and stirred at 70° C. overnight to obtain a compound 9. The yield of the compound 9 is 85%.

MS (MALDI-TOF-MS, m/z) 890.23 (M+)

Synthesis of Compound 10 (Second Intermediate)

4.1 g (4.6 mmol) of the compound 9 and 400 ml of tetrahydrofuran are put in a flask and the mixture is stirred. Then, 2.24 g (9.2 mmol) of iodine (I$_2$) is added thereto and the mixture is stirred overnight. Subsequently, a methanol is added thereto and filtered to obtain a compound 10. The yield of the compound 10 is 75%.

MS (MALDI-TOF-MS, m/z) 1002.15 (M+)

Synthesis of Compound 11 (Final Product)

3.4 g (3.4 mmol) of the compound 10, 0.13 g (0.68 mmol) of copper iodide, 0.33 g (10.2 mmol) of sulfur powder and 0.59 g (4.3 mmol) of calcium carbonate (K$_2$CO$_3$) are put in a flask. Then, 300 ml of dimethylformamide is added thereto and the mixture is stirred at 110° C. overnight. Subsequently, after cooling to 0° C., the extraction is performed to obtain a crude product. Then, the crude product is suspended with a mixed solvent of dimethylacetamide and water, filtered, and washed with water, acetone, and tetrahydrofuran to obtain a compound 11. The yield is 93%.

MS (MALDI-TOF-MS, m/z) 828.11 (M+)

Synthesis Example 4

[Reaction Scheme 4]

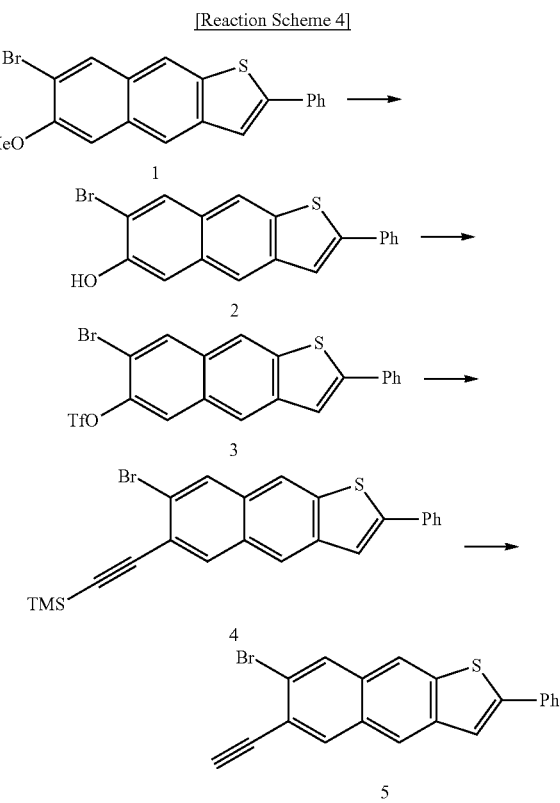

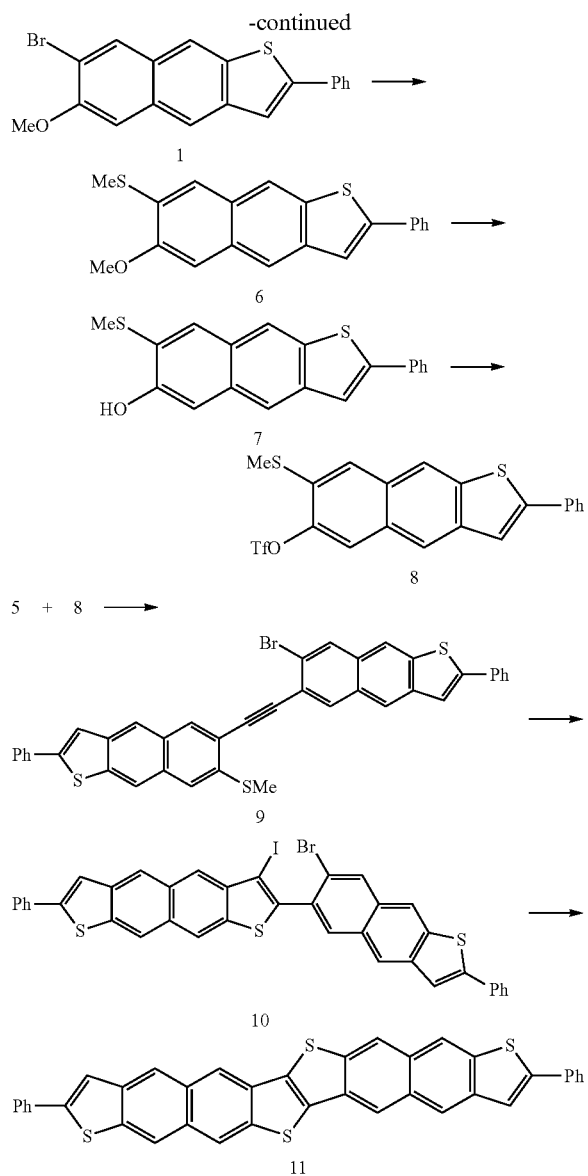

Synthesis of Compound 2:

2.0 g (5.5 mmol) of the compound 1 is put in a flask and dissolved in 1 L of dichloromethane (CH$_2$Cl$_2$). After cooling, 19 mL (19.3 mmol) of 1M tribromoboron (BBr$_3$) solution is added thereto, and the obtained mixture is additionally stirred for 4 hours. Then, a saturated ammonium chloride solution is added thereto and then the extraction is performed with chloroform. Then, the resultant is dried with anhydrous magnesium sulfate, filtered and removed remaining solvent to obtain a compound 2 of yellow solid. The yield is 92%.

NMR (CDCl$_3$, 300 MHz) 5.59 (s, 1H), 7.43 (m, 3H), 7.59 (s, 1H), 7.61 (s, 1H), 7.76 (m, 2H), 8.09 (s, 1H), 8.10 (s, 1H), 8.16 (s, 1H).

Synthesis of Compound 3:

1.78 g (5.0 mmol) of the compound 2 is put in a flask and dissolved in 1 L of dichloromethane (CH$_2$Cl$_2$). Subsequently, 1.9 mL (13.5 mmol) of triethylamine (NEt$_3$) is added thereto, 1.3 mL (7.5 mmol) of trifluoromethansulfonic anhydride (Tf$_2$O) is added thereto at 0° C., and the obtained mixture is additionally stirred overnight. Then, a saturated ammonium chloride solution and water are added thereto. Subsequently, a water layer is separated and the extraction is performed with dichloromethane. Subsequently, an organic layer therefrom is washed with a saturated saline solution, dried and concentrated with anhydrous magnesium sulfate, and purified through column chromatography to obtain a compound 3. The yield of the compound 3 is 60%.

NMR (CDCl$_3$, 300 MHz) 7.46 (m, 3H), 7.65 (s, 1H), 7.78 (m, 2H), 7.93 (s, 1H), 8.23 (s, 1H), 8.26 (s, 1H), 8.28 (s, 1H).

Synthesis of Compounds 4 and 5:

1.47 g (3.0 mmol) of the compound 3, 190 mL of dimethyl formamide (DMF), and 40 mL (286 mmol) of triethylamine (NEt$_3$) are put in a flask. Subsequently, 4.5 mL (0.65 mmol) of trimethylsilylacetylene (TMSA), 60 mg (0.3 mmol) of copper iodide and 110 mg (0.15 mmol) of palladium bis(triphenylphosphine)dichloride Pd(PPh$_3$)$_2$Cl$_2$ are added thereto, and the mixture is stirred overnight. Then, a saturated ammonium chloride solution and water are added thereto, and a water layer is extracted with dichloromethane. Subsequently, an organic layer therefrom is washed with a saline solution, dried with anhydrous magnesium sulfate, and purified through column chromatography to obtain a crude product. The crude product is suspended in 100 mL of methanol (MeOH), 0.84 g (14.9 mmol) of potassium hydroxide (KOH) is added thereto. Subsequently, the mixture is stirred for 4 hours, and water is added thereto to precipitate a solid to obtain a compound 5. The yield of the compound 5 is 66%.

NMR (CDCl$_3$, 300 MHz) 3.41 (s, 1H), 7.45 (m, 3H), 7.64 (s, 1H), 7.76 (m, 2H), 8.02 (s, 1H), 8.14 (s, 1H), 8.20 (d, 2H).

Synthesis of Compound 6:

9.1 g (24.6 mmol) of the compound 1, 2.3 g (31.9 mmol) of sodium thiomethoxide (NaSMe), 4.4 g (31.9 mmol) of potassium carbonate (K$_2$CO$_3$), 2.3 g (2.5 mmol) of tris(dibenzylideneacetone)dipalladium(0), and 2.7 g (4.9 mmol) of bis[2-(diphenylphosphino)phenyl]ether are put in a flask and added 1 L of toluene, and then stirred for 24 hours at 110° C. After cooling, sodium hydrogen carbonate is added thereto, and the extraction is performed with toluene. Subsequently, the resultant is dried with anhydrous magnesium sulfate, filtered, and an organic solvent is removed under vacuum. Then, the resultant is purified through silica gel column chromatography (solvent: hexane and chloroform) to obtain a compound 6 of white solid. The yield of the compound 6 is 99%.

NMR (CDCl$_3$, 300 MHz) 2.57 (s, 3H), 4.03 (m, 3H), 7.16 (s, 1H), 7.43 (m, 3H), 7.60 (s, 1H), 7.76 (m, 2H), 8.11 (s, 1H), 8.16 (s, 1H).

Synthesis of Compound 7

8.3 g (24.6 mmol) of the compound 6 and 1.5 L of dichloromethane are put in a flask. After cooling, 37 ml (37 mmol) of 1M tribromoboron (BBr$_3$) solution is added thereto, and the mixture is stirred for 4 hours. Then, a saturated ammonium chloride solution is added thereto, and the extraction is performed with chloroform. Subsequently, an organic layer therefrom is dried with anhydrous magnesium sulfate, and filtered to obtain a compound 7 of yellow solid. The yield of the compound 7 is 86%.

NMR (CDCl$_3$, 300 MHz) 2.47 (s, 3H), 6.56 (s, 1H), 7.43 (m, 3H), 7.59 (s, 1H), 7.76 (m, 2H), 8.06 (s, 1H), 8.10 (s, 1H), 8.18 (s, 1H).

Synthesis of Compound 8

6.8 g (21.1 mmol) of the compound 7 and 3 L of dichloromethane (CH$_2$Cl$_2$) are put in a flask and the mixture is stirred. Subsequently, 8.1 mL (56.8 mmol) of triethylamine is added thereto, and then 5.3 mL (31.6 mmol) of trifluoromethansulfonic anhydride (Tf$_2$O) is added thereto at 0° C., and the obtained mixture is additionally stirred overnight. Then, a saturated ammonium chloride solution and water are added thereto. Subsequently, a water layer is separated and the extraction is performed with dichloromethane. Subsequently, an organic layer therefrom is washed with a saturated saline solution, dried and concentrated with anhydrous magnesium sulfate, and purified through column chromatography to obtain a compound 8. The yield of the compound 8 is 69%.

NMR (CDCl$_3$, 300 MHz) 2.63 (s, 3H), 6.56 (s, 1H), 7.43 (m, 3H), 7.59 (s, 1H), 7.76 (m, 2H), 8.06 (s, 1H), 8.10 (s, 1H), 8.18 (s, 1H).

Synthesis of Compound 9 (First Intermediate)

3.3 g (7.3 mmol) of the compound 8, 425 mL of dimethyl formamide (DMF), 210 mg (1.1 mmol) of copper iodide, 160 mg (0.22 mmol) of palladium(0) bis(triphenylphosphine)dichloride (Pd(PPh$_3$)$_2$Cl$_2$), 1.86 g (11.2 mmol) of potassium iodide (KI), 85 ml of triethylamine (NEt$_3$) and 425 ml of dimethylformamide (DMF) are put in a flask and the mixture is stirred for 15 minutes. Then, 2.64 g (7.3 mmol) of the compound 5 is added thereto and stirred at 70° C. overnight to obtain a compound 9. The yield of the compound 9 is 83%.

MS (MALDI-TOF-MS, m/z) 665.95 (M+)

Synthesis of Compound 10 (Second Intermediate)

8.1 g (12.1 mmol) of the compound 9 and 800 ml of tetrahydrofuran are put in a flask and the mixture is stirred. Then, 9.2 g (36.4 mmol) of iodine (12) is added thereto and the mixture is stirred overnight. Subsequently, a methanol is added thereto and filtered to obtain a compound 10. The yield of the compound 10 is 87%.

MS (MALDI-TOF-MS, m/z) 777.83 (M+)

Synthesis of Compound 11 (Final Product)

8.2 g (10.5 mmol) of the compound 10, 0.4 g (2.1 mmol) of copper iodide, 1.01 g (31.6 mmol) of sulfur powder and 4.36 g (31.6 mmol) of calcium carbonate (K$_2$CO$_3$) are put in a flask. Then, 820 ml of N-methylpyrrolidone (NMP) is added thereto and the mixture is stirred at 130° C. overnight. Subsequently, after cooling to 0° C., the extraction is performed to obtain a crude product. Then, the crude product is suspended with a mixed solvent of dimethylacetamide and water, filtered, and washed with water, acetone, and tetrahydrofuran to obtain a compound 11. The yield is 75%.

MS (MALDI-TOF-MS, m/z) 603.98 (M+)

Manufacture of Organic Thin Film Transistor

A silicon wafer substrate coated with the cleaned SiO$_2$ to be 3000 Å thick is exposed to O$_2$ plasma and then, dipped in an octadecyl trichlorosilane solution diluted in hexane to a concentration of 5 mM to change the surface to be hydrophobic. Subsequently, the fused heteroaromatic compound according to Synthesis Example 1 is vacuum-vapor deposited to be 700 Å thick by heating the substrate from room temperature to 200° C. Then, source and drain electrodes are formed thereon by using a shadow mask and depositing Au to be 1000 Å thick to manufacture an organic thin film transistor.

Charge mobility of the organic thin film transistor is calculated.

The charge mobility of the organic thin film transistor is obtained by obtaining a graph having (ISD)1/2 and V$_G$ as variables from a saturation region current equation and a slope in the graph.

$$I_{SD} = \frac{WC_0}{2L}\mu(V_G - V_T)^2$$

$$\sqrt{I_{SD}} = \sqrt{\frac{\mu C_0 W}{2L}}(V_G - V_T)$$

$$\text{slope} = \sqrt{\frac{\mu C_0 W}{2L}}$$

$$\mu_{FET} = (\text{slope})^2 \frac{2L}{C_0 W}$$

In the equations, ISD is a source-drain current, μ or μFET is charge mobility, C0 is electrostatic capacity of a gate insulating layer, W is a channel width, L is a channel length, VG is a gate voltage, and VT is a threshold voltage.

A cut-off leakage current (Ioff) is obtained as a minimum current in an off state as a current flowing in an off state. A current on-off ratio (Ion/Ioff) is obtained as a ratio of a maximum current in an on state relative to a minimum current in the off state.

The charge mobility of the organic thin film transistor exhibits relatively high charge mobility of about 13 cm$^2$/Vs.

While this disclosure has been described in connection with what is presently considered to be practical example embodiments, it is to be understood that the inventive concepts are not limited to the disclosed embodiments, but, on the contrary, is intended to cover various modifications and equivalent arrangements included within the spirit and scope of the appended claims.

What is claimed is:

1. An intermediate represented by Chemical Formula 3b:

[Chemical Formula 3b]

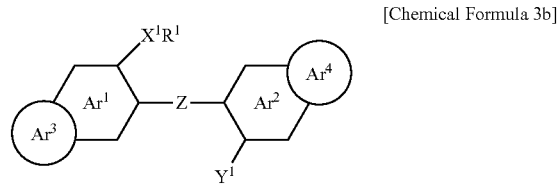

wherein, in Chemical Formula 3b,
each of Ar$^1$ and Ar$^2$ are independently a substituted or unsubstituted aromatic ring,
each of Ar$^3$ and Ar$^4$ are independently a substituted or unsubstituted heteroaromatic ring,
X$^1$ is a chalcogen element,
R$^1$ is one of hydrogen, a substituted or unsubstituted C$_1$ to C$_{20}$ alkyl group, a C$_1$ to C$_{20}$ fluoroalkyl group, a substituted or unsubstituted C$_6$ to C$_{20}$ aryl group, a halogen, and a combination thereof,
Z is one of an ethene group and an ethyne group,
Y$^1$ is a halogen, and
Y$^1$ and X$^1$ are bonded to β-carbon positions in Ar$_1$ and Ar$_2$, respectively, that are adjacent to Z.

2. The intermediate of claim 1, wherein
the Ar$^1$ and Ar$^2$ groups are independently a phenyl group, a naphthyl group, an anthracenyl group, a tetracenyl group, or a pentacenyl group, and
the Ar$^3$ and Ar$^4$ groups are independently a thiophenyl group, a selenophenyl group, a tellurophenyl group, a furanyl group, or a pyrrolyl group.

3. The intermediate of claim 1, wherein in Chemical Formula 3b,
Y$^1$ is a bromine,
Z is an ethyne group,
each of Ar$^1$ and Ar$^2$ are independently a naphthyl group, an anthracenyl group, a tetracenyl group, or a pentacenyl group, each $Ar^3$ and $Ar^4$ are a thiophenyl group, a selenophenyl group, a tellurophenyl group, a furanyl group, a pyrrolyl group, and a fused ring of two or more rings therefrom, $X^1$ is a chalcogen element, and $R^1$ is one of hydrogen, a substituted or unsubstituted $C_1$ to $C_{20}$ alkyl group, a $C_1$ to $C_{20}$ fluoroalkyl group, a substituted or unsubstituted $C_6$ to $C_{20}$ aryl group, a halogen, and a combination thereof.

4. The intermediate of claim 2, wherein the $Ar^3$ and $Ar^4$ groups are a thiophenyl group.

5. The intermediate of claim 2, wherein the $Ar^3$ and $Ar^4$ groups are a selenophenyl group.

6. The intermediate of claim 2, wherein the $Ar^3$ and $Ar^4$ groups are a tellurophenyl group.

7. The intermediate of claim 2, wherein the $Ar^3$ and $Ar^4$ groups are a furanyl group.

8. The intermediate of claim 2, wherein the $Ar^3$ and $Ar^4$ groups are a pyrrolyl group.

9. The intermediate of claim 2, wherein the Z is an ethene group.

10. The intermediate of claim 2, wherein the Z is an ethyne group.

11. The intermediate of claim 3, wherein the $X^1$ is S.

12. The intermediate of claim 11, wherein the $R^1$ is a methyl group.

* * * * *